(12) United States Patent
Vuckovic

(10) Patent No.: US 11,110,113 B2
(45) Date of Patent: Sep. 7, 2021

(54) COMPOSITIONS AND METHODS FOR TREATING DEPRESSION

(71) Applicant: Gentelon, Inc., Carlisle, MA (US)

(72) Inventor: Alexander Vuckovic, Carlisle, MA (US)

(73) Assignee: Gentelon, Inc., Carlisle, MA (US)

( * ) Notice: Subject to any disclaimer, the term of this patent is extended or adjusted under 35 U.S.C. 154(b) by 0 days.

(21) Appl. No.: 16/347,156

(22) PCT Filed: Nov. 3, 2017

(86) PCT No.: PCT/US2017/059819
§ 371 (c)(1),
(2) Date: May 2, 2019

(87) PCT Pub. No.: WO2018/144088
PCT Pub. Date: Aug. 9, 2018

(65) Prior Publication Data
US 2020/0179429 A1 Jun. 11, 2020

Related U.S. Application Data

(60) Provisional application No. 62/417,229, filed on Nov. 3, 2016.

(51) Int. Cl.
| A61K 31/7076 | (2006.01) |
| A61K 31/202 | (2006.01) |
| A61K 31/519 | (2006.01) |
| A61K 31/593 | (2006.01) |
| A61K 31/685 | (2006.01) |

(52) U.S. Cl.
CPC ........ *A61K 31/7076* (2013.01); *A61K 31/202* (2013.01); *A61K 31/519* (2013.01); *A61K 31/593* (2013.01); *A61K 31/685* (2013.01)

(58) Field of Classification Search
CPC . A61K 31/7076; A61K 31/202; A61K 31/519
See application file for complete search history.

(56) References Cited

U.S. PATENT DOCUMENTS

| 5,059,595 A | 10/1991 | Le Grazie |
| 5,538,734 A | 7/1996 | Le Grazie |
| 6,011,040 A | 1/2000 | Muller et al. |
| 6,020,139 A | 2/2000 | Schwartz et al. |
| 6,093,703 A | 7/2000 | La Greca |
| 6,254,904 B1 | 7/2001 | Bailey |
| 6,271,374 B1 | 8/2001 | Muller et al. |
| 6,441,168 B1 | 8/2002 | Muller et al. |
| 6,514,973 B1 | 2/2003 | Buchholz et al. |
| 6,544,547 B2 | 4/2003 | Hageman |
| 6,596,701 B1 | 7/2003 | Schwartz et al. |
| 6,673,381 B2 | 1/2004 | Bailey et al. |
| 6,800,725 B2 | 10/2004 | Hofman et al. |
| 6,808,725 B2 | 10/2004 | Bailey et al. |
| 6,921,754 B2 | 7/2005 | Hahnlein et al. |
| 7,208,180 B2 * | 4/2007 | Kiliaan ............... A61K 36/16 424/725 |
| 7,429,569 B2 | 9/2008 | Halevie-Goldman |
| 7,674,490 B2 | 3/2010 | Bailey et al. |
| 7,712,778 B2 | 5/2010 | Smith et al. |
| 8,372,451 B2 | 2/2013 | Vuckovic |
| 9,662,359 B2 * | 5/2017 | Vuckovic ............... A23L 33/12 |
| 2001/0019724 A1 | 9/2001 | Runge et al. |
| 2002/0044991 A1 | 4/2002 | Auweter et al. |
| 2002/0110599 A1 | 8/2002 | Auweter et al. |
| 2002/0182196 A1 | 12/2002 | McCleary |
| 2003/0148991 A1 | 8/2003 | Hahnlein et al. |
| 2003/0185877 A1 | 10/2003 | Betz et al. |
| 2004/0043013 A1 | 3/2004 | McCleary |

(Continued)

FOREIGN PATENT DOCUMENTS

| EP | 1 275 399 B1 | 8/2008 |
| WO | WO 1999/037155 A1 | 7/1999 |

(Continued)

OTHER PUBLICATIONS

Kim ; Progress in Lipid Research Oct. 2015, pp. 1-45.*
Extended European Search Report, dated Nov. 28, 2013, in connection with Application No. EP 11742864.9.
International Search Report and Written Opinion, dated Oct. 25, 2011, in connect with Application No. PCT/US2011/024530.
International Preliminary Report on Patentability, dated Aug. 23, 2012, in connect with Application No. PCT/US2011/024530.
International Search Report and Written Opinion, dated Jul. 13, 2018, in connection with Application No. PCT/US2017/059819.
International Preliminary Report on Patentability, dated May 16, 2019, in connection with Application No. PCT/US2017/059819.
Office Communication, dated Feb. 24, 2012, for U.S. Appl. No. 13/025,928.

(Continued)

*Primary Examiner* — Pancham Bakshi
(74) *Attorney, Agent, or Firm* — Wolf, Greenfield & Sacks, P.C.

(57) ABSTRACT

Disclosed is a therapeutic regimen which includes S-adenosyl methionine, or a salt thereof; folic acid, or a metabolite therof, or a salt thereof; and a compound of Formula (I), or salt thereof, useful in the treatment of a variety of conditions, e.g., neuropsychiatric conditions such as depression. The therapeutic regimen may be used in combination with therapeutic agents as described here.

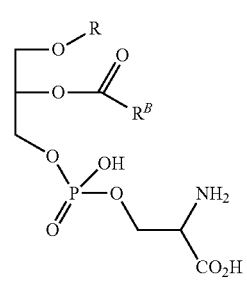

(I)

21 Claims, No Drawings

(56) References Cited

U.S. PATENT DOCUMENTS

| | | |
|---|---|---|
| 2004/0157783 A1 | 8/2004 | McCaddon |
| 2004/0241285 A1 | 12/2004 | Habich et al. |
| 2005/0147665 A1 | 7/2005 | Horrobin et al. |
| 2005/0267212 A1 | 12/2005 | Stoll |
| 2006/0188607 A1 | 8/2006 | Schramm et al. |
| 2007/0042008 A1 | 2/2007 | Kane et al. |
| 2007/0082044 A1 | 4/2007 | Yeum |
| 2008/0038367 A1 | 2/2008 | Saloum |
| 2008/0213239 A1 | 9/2008 | Morris |
| 2008/0214492 A1 | 9/2008 | Hendrix |
| 2008/0274175 A1 | 11/2008 | Schramm et al. |
| 2010/0087546 A1 | 4/2010 | Appleton |
| 2011/0200690 A1 | 8/2011 | Vuckovic |
| 2013/0295203 A1* | 11/2013 | Lombard ............... A23L 33/10 424/682 |
| 2013/0330429 A1 | 12/2013 | Vuckovic |
| 2018/0104294 A1 | 4/2018 | Vuckovic |

FOREIGN PATENT DOCUMENTS

| | | |
|---|---|---|
| WO | WO 2005/109175 A2 | 11/2005 |
| WO | WO 2009/158430 A1 | 12/2009 |
| WO | WO 2011/012989 A1 | 2/2011 |

OTHER PUBLICATIONS

Office Communication, dated Apr. 12, 2012, for U.S. Appl. No. 13/025,928.

Office Communication, dated Jun. 1, 2012, for U.S. Appl. No. 13/025,928.

Advisory Action, dated Jul. 11, 2012, for U.S. Appl. No. 13/025,928.

Notice of Allowance, dated Dec. 19, 2012 for U.S. Appl. No. 13/025,928.

Supplemental Notice of Allowance, dated Jan. 2, 2013, for U.S. Appl. No. 13/025,928.

[No Author Listed] 5-methyltetrahydrofolate. Monograph. Altern Med Rev. Dec. 2006;11(4):330-7.

[No Author Listed] Compared with fluoxetine monotherapy, mirtazapine plus venlafaxine or fluoxetine increase remission but not response in patients with major depressive disorder. Evid Based Mental Health. Epublication. Last accessed on Nov. 19, 2010 at http://ebmh.bmj.com/content/early/2010/07/22/ebmh1061.full. 2 pages.

[No Author Listed] Deplin® Tablets. Package Insert. PAMLAB, L.L.C. Covington, LA. Revised Feb. 2010. 1 page.

[No Author Listed] Facts about Folate. Eat Right Ontario. Government of Ontario. Last accessed on May 31, 2011 at www.eatrightontario.ca/en/ViewDocument.aspx?id=109. 3 pages.

[No Author Listed] Omega-e Fatty Acids in Mood Disorders. Psychiatry Drug Alerts. Nov. 2009;23(11):79-86.

[No Author Listed] Quetiapine/Ritonavir: Clinically Significant Interaction. Psychiatry Drug Alerts. Dec. 2009;23(12):87-94.

[No Author Listed] S-Adenosyl-L-Methionine for Treatment of Depression, Osteoarthritis, and Liver Disease. Evidence Reports/Technology Assessments. Oct. 2002, No. 64. Rockville, Maryland. Agency for Healthcare Research and Quality. Last accessed on Jan. 27, 2012 at http://www.ncbi.nlm.nih.gov/books/NBK36942/. Structured Abstract. 3 pages.

[No Author Listed] S-Adenosylmethionine. University of Maryland Medical Center. Reviewed last on Dec. 7, 2009 by Steven Ehrlich. Last accessed on Jan. 27, 2012 at http://www.umm.edu/altmed/articles/s-adenosylmethionine-000324.htm. 6 pages.

Alpert et al., Nutrition and depression: the role of folate. Nutr Rev. May 1997;55(5):145-9.

Antoniades et al., MTHFR 677 C>T Polymorphism reveals functional importance for 5-methyltetrahydrofolate, not homocysteine, in regulation of vascular redox state and endothelial function in human atherosclerosis. Circulation. May 12, 2009;119(18):2507-15. Epub Apr. 27, 2009.

Bailey et al., The extremely slow and variable activity of dihydrofolate reductase in human liver and its implications for high folic acid intake. Proc Natl Acad Sci U S A. Sep. 8, 2009;106(36):15424-9. Epub Aug. 24, 2009.

Behzadi et al., Folic acid efficacy as an alternative drug added to sodium valproate in the treatment of acute phase of mania in bipolar disorder: a double-blind randomized controlled trial. Acta Psychiatr Scand. Dec. 2009;120(6):441-5. Epub Mar. 10, 2009.

Bottiglieri, Ademetionine (S-adenosylmethionine) neuropharmacology: implications for drug therapies in psychiatric and neurological disorders. Expert Opin Investig Drugs. Apr. 1997;6(4):417-26.

Bottiglieri, Homocysteine and folate metabolism in depression. Prog Neuropsychopharmacol Biol Psychiatry. Sep. 2005;29(7):1103-12.

Calabrese et al., Fish oils and bipolar disorder: a promising but untested treatment. Arch Gen Psychiatry. May 1999;56(5):413-4; discussion 415-6.

Coppen et al., Enhancement of the antidepressant action of fluoxetine by folic acid: a randomised, placebo controlled trial. J Affect Disord. Nov. 2000;60(2):121-30.

Coppen et al., Treatment of depression: time to consider folic acid and vitamin B12. J Psychopharmacol. Jan. 2005;19(1):59-65.

Di Palma et al., Is methylfolate effective in relieving major depression in chronic alcoholics? A hypothesis of treatment. Current Therapeutic Research. May 1994;55:559-568.

Farah, the role of L-methylfolate in depressive disorders. CNS Spectr. Jan. 2009;14(1 Suppl 2):2-7.

Fava et al., Folate in depression: efficacy, safety, differences in formulations, and clinical issues. J Clin Psychiatry. 2009;70 Suppl 5:12-7.

Fetrow et al., Efficacy of the dietary supplement S-adenosyl-L-methionine. Ann Pharmacother. Nov. 2001;35(11):1414-25.

Figueiredo et al., Folic acid and risk of prostate cancer: results from a randomized clinical trial. J Natl Cancer Inst. Mar. 18, 2009;101(6):432-5. Epub Mar. 10, 2009.

Freeman et al., Complementary and alternative medicine for major depressive disorder: a meta-analysis of patient characteristics, placebo-response rates, and treatment outcomes relative to standard antidepressants. J Clin Psychiatry. Jun. 2010;71(6):682-8.

Freeman et al., Complementary and alternative medicine in major depressive disorder: the American Psychiatric Association Task Force report. J Clin Psychiatry. Jun. 2010;71(6):669-81.

Freeman et al., Omega-3 fatty acids: evidence basis for treatment and future research in psychiatry. J Clin Psychiatry. Dec. 2006;67(12):1954-67.

Freeman, Complementary and Alternative Medicine (CAM): considerations for the treatment of major depressive disorder. J Clin Psychiatry. 2009;70 Suppl 5:4-6.

Freeman, Omega-3 fatty acids or salts thereof in Major Depressive disorder. J Clin Psychiatry. 2009;70 Suppl 5:7-11.

Fugh-Berman et al., Dietary supplements and natural products as psychotherapeutic agents. Psychosom Med. Sep.-Oct. 1999;61(5):712-28.

Galbiatti et al., 5-Methyltetrahydrofolate-homocysteine methyltransferase gene polymorphism (MTR) and risk of head and neck cancer. Braz J Med Biol Res. May 2010;43(5):445-50. Epub Apr. 23, 2010.

Gelenberg, Complementary and alternative medicine in psychiatry. J Clin Psychiatry. Jun. 2010;71(6):667-8.

Gilbody et al., Methylenetetrahydrofolate reductase (MTHFR) genetic polymorphisms and psychiatric disorders: a HuGE review. Am J Epidemiol. Jan. 1, 2007;165(1):1-13. Epub Oct. 30, 2006.

Godfrey et al., Enhancement of recovery from psychiatric illness by methylfolate. Lancet. Aug. 18, 1990;336(8712):392-5.

Green et al., Red cell membrane omega-3 fatty acids are decreased in nondepressed patients with social anxiety disorder. Eur Neuropsychopharmacol. Feb. 2006;16(2):107-13. Epub Oct. 21, 2005.

Guaraldi et al., An open trial of methyltetrahydrofolate in elderly depressed patients. Ann Clin Psychiatry. Jun. 1993;5(2):101-5.

Guthikonda et al., Homocysteine: role and implications in atherosclerosis. Curr Atheroscler Rep. Mar. 2006;8(2):100-6.

(56) References Cited

OTHER PUBLICATIONS

Hayden et al., Homocysteine and reactive oxygen species in metabolic syndrome, type 2 diabetes mellitus, and atheroscleropathy: the pleiotropic effects of folate supplementation. Nutr J. May 10, 2004;3:4.
Huan et al., Suicide attempt and n-3 fatty acid levels in red blood cells: a case control study in China. Biol Psychiatry. Oct. 1, 2004;56(7):490-6.
Iso et al., Intake of fish and omega-3 fatty acids and risk of stroke in women. JAMA. Jan. 17, 2001;285(3):304-12.
Kagan et al., Oral S-adenosylmethionine in depression: a randomized, double-blind, placebo-controlled trial. Am J Psychiatry. May 1990;147(5):591-5.
Kelly et al., The MTHFR C677T polymorphism is associated with depressive episodes in patients from Northern Ireland. J Psychopharmacol. Dec. 2004;18(4):567-71.
Knowlton et al., Investigating SAM-e. Geriatric Times. Sep./Oct. 2001;2(5): 3 pages. Last accessed on May 20, 2011 at http://www.geriatrictimes.com/g010923.html.
Kris-Etherton et al., Fish consumption, fish oil, omega-3 fatty acids, and cardiovascular disease. American Heart Association. Nutrition Committee. Circulation. Nov. 19, 2002;106(21):2747-57. Erratum in: Circulation. Jan. 28, 2003;107(3):512.
Lieber et al., S-Adenosylmethionine: molecular, biological, and clinical aspects—an introduction. Am J Clin Nutr. 2002;76(5):1148S-50S and Supplemental Information. doi:10.1093/ajcn/76/5.1148S.
Lin et al., A meta-analytic review of double-blind, placebo-controlled trials of antidepressant efficacy of omega-3 fatty acids. J Clin Psychiatry. Jul. 2007;68(7):1056-61.
Linde et al., St. John's wort for major depression (review). The Cochrane collaboration. Wiley. 2008;4. 110 pages.
Loehrer et al., Influence of oral S-adenosylmethionine on plasma 5-methyltetrahydrofolate, S-adenosylhomocysteine, homocysteine and methionine in healthy humans. J Pharmacol Exp Ther. Aug. 1997;282(2):845-50.
Mischoulon et al., A double-blind, randomized controlled trial of ethyl-eicosapentaenoate for major depressive disorder. J Clin Psychiatry. Dec. 2009;70(12):1636-44. Epub Aug. 25, 2009.
Mischoulon et al., Are nutritional supplements ready for prime time? J Clin Psychiatry. Sep. 2008;69(9):1497-8.
Mischoulon et al., Role of S-adenosyl-L-methionine in the treatment of depression: a review of the evidence. Am J Clin Nutr. Nov. 2002;76(5):1158S-61S.
Morrison et al., Brain S-adenosylmethionine levels are severely decreased in Alzheimer's disease. J Neurochem. Sep. 1996;67(3):1328-31.
Najm et al., S-adenosyl methionine (SAMe) versus celecoxib for the treatment of osteoarthritis symptoms: a double-blind cross-over trial. [ISRCTN36233495]. BMC Musculoskelet Disord. Feb. 26, 2004;5:6. 15 pages.
Naliwaiko et al., Effects of fish oil on the central nervous system: a new potential antidepressant? Nutr Neurosci. Apr. 2004;7(2):91-9.
Nemets et al., Addition of omega-3 fatty acid to maintenance medication treatment for recurrent unipolar depressive disorder. Am J Psychiatry. Mar. 2002;159(3):477-9.
Nemets et al., Omega-3 treatment of childhood depression: a controlled, double-blind pilot study. Am J Psychiatry. Jun. 2006;163(6):1098-100.
Obeid et al., Homocysteine and lipids: S-adenosyl methionine as a key intermediate. FEBS Lett. Apr. 17, 2009;583(8):1215-25. doi:10.1016/j.febslet.2009.03.038. Epub Mar. 25, 2009. Review. Erratum in: FEBS Lett. Sep. 17, 2009;583(18):3107.
Papakostas et al., S-adenosyl methionine (SAMe) augmentation of serotonin reuptake inhibitors for antidepressant nonresponders with major depressive disorder: a double-blind, randomized clinical trial. Am J Psychiatry. Aug. 2010;167(8):942-8. Epub Jul. 1, 2010.
Papakostas, Evidence for S-adenosyl-L-methionine (SAM-e) for the treatment of major depressive disorder. J Clin Psychiatry. 2009;70 Suppl 5:18-22.
Passeri et al., Oral 5'-methyltetrahydrofolic acid in senile organic mental disorders with depression: results of a double-blind multi-center study. Aging (Milano). Feb. 1993;5(1):63-71.
Price et al., Neurology and psychiatry: closing the great divide. Neurology. Jan. 11, 2000;54(1):8-14.
Puri, The use of eicosapentaenoic acid in the treatment of chronic fatigue syndrome. Prostaglandins Leukot Essent Fatty Acids. Apr. 2004;70(4):399-401.
Rizos et al., Association between omega-3 fatty acid supplementation and risk of major cardiovascular disease events: a systematic review and meta-analysis. JAMA. Sep. 12, 2012;308(10):1024-33. doi: 10.1001/2012.jama.11374.
Rosenbaum et al., The antidepressant potential of oral S-adenosyl-1-methionine. Acta Psychiatr Scand. May 1990;81(5):432-6.
Ross et al., Omega-3 fatty acids as treatments for mental illness: which disorder and which fatty acid? Lipids Health Dis. Sep. 18, 2007;6:21.
Sarris et al., Adjunctive Nutraceuticals for Depression: A Systematic Review and Meta-Analyses. Am J Psychiatry. Jun. 1, 2016;173(6):575-87. doi: 10.1176/appi.ajp.2016.15091228. Epub Apr. 26, 2016.
Sarris et al., Major depressive disorder and nutritional medicine: a review of monotherapies and adjuvant treatments. Nutr Rev. Mar. 2009;67(3):125-31. doi: 10.1111/j.1753-4887.2009.00180.x.
Shelton, Commentary. Prim psychiatry. Jan. 2009;16(1):8.
Shelton, St John's wort (*Hypericum perforatum*) in major depression. J Clin Psychiatry. 2009;70 Suppl 5:23-7.
Stahl, Enhancing outcomes from major depression: using antidepressant combination therapies with multifunctional pharmacologic mechanisms from the initiation of treatment. CNS Spectr. Feb. 2010;15(2):79-94.
Stahl, L-methylfolate: a vitamin for your monoamines. J Clin Psychiatry. Sep. 2008;69(9):1352-3.
Stahl, Novel therapeutics for depression: L-methylfolate as a trimonoamine modulator and antidepressant-augmenting agent. CNS Spectr. Oct. 2007;12(10):739-44.
Stanger et al.,Homocysteine, folate and vitamin B12 in neuropsychiatric diseases: review and treatment recommendations. Expert Rev Neurother. Sep. 2009;9(9):1393-412. doi: 10.1586/ern.09.75.
Stewart et al., Does dual antidepressant therapy as initial treatment hasten and increase remission from depression? J Psychiatr Pract. Sep. 2009;15(5):337-45.
Stoll et al., Omega 3 fatty acids in bipolar disorder: a preliminary double-blind, placebo-controlled trial. Arch Gen Psychiatry. May 1999;56(5):407-12.
Su et al., Omega-3 fatty acids in major depressive disorder. A preliminary double-blind, placebo-controlled trial. Eur Neuropsychopharmacol. Aug. 2003;13(4):267-71.
Taylor et al., Folate for depressive disorders: systematic review and meta-analysis of randomized controlled trials. J Psychopharmacol. Jun. 2004;18(2):251-6.
Trivedi, The good, the fad, and the unhealthy. New Scientist. Sep. 2006:42-9.
Ural, Folic Acid and Pregnancy. Kid's Health. Last accessed on May 31, 2011 at http://kidshealth.org/parent/pregnancy_newborn/pregnancy/folic_acid.html. 2 pages.
Volker et al., Omega-3 Fatty acids, tryptophan, B vitamins, SAMe, and Hypericum in the adjunctive treatment of depression. In: Handbook of nutraceuticals and functional foods. 2007. Chapter 19. 373-390.
Weinstein et al., Null association between prostate cancer and serum folate, vitamin B(6), vitamin B(12), and homocysteine. Cancer Epidemiol Biomarkers Prev. Nov. 2003;12(11 Pt 1):1271-2.
Yehuda et al., Mixture of essential fatty acids lowers test anxiety. Nutr Neurosci. Aug. 2005;8(4):265-7.
U.S. Appl. No. 13/025,928, filed Feb. 1, 2011, Vuckovic.
U.S. Appl. No. 13/763,792, filed Feb. 11, 2013, Vuckovic.
U.S. Appl. No. 15/606,872, filed May 26, 2017, Vuckovic.
EP 11742864.9, Nov. 28, 2013, Extended European Search Report.
PCT/US2011/024530, Oct. 25, 2011, International Search Report and Written Opinion.
PCT/US2011/024530, Aug. 23, 2012, International Preliminary Report on Patentability.

(56) References Cited

OTHER PUBLICATIONS

PCT/US2017/059819, Jul. 13, 2018, International Search Report and Written Opinion.
PCT/US2017/059819, May 16, 2019, International Preliminary Report on Patentability.

\* cited by examiner

COMPOSITIONS AND METHODS FOR TREATING DEPRESSION

RELATED APPLICATIONS

This application is a national stage filing under 35 U.S.C. § 371 of International PCT Application, PCT/US2017/059819, filed Nov. 3, 2017, which claims priority under 35 U.S.C. § 119(e) to U.S. Provisional Application, U.S. Ser. No. 62/417,229, filed Nov. 3, 2016, the entire contents of each of which is incorporated herein by reference.

BACKGROUND

Behavioral neurology is a subspecialty of neurology that studies the neurological basis of behavior, memory, and cognition, the impact of neurological damage and disease upon these functions, and the treatment thereof (see, e.g., Pincus and Tucker, *Behavioral Neurology* ($2^{nd}$ Edition), Oxford University Press, 1979). Neuropsychiatry is a closely related branch of medicine dealing with mood and mental disorders attributable to diseases of the nervous system (see, e.g., Price et al., *Neurology* (2000) 54:8-14). Both fields are involved in treating conditions which are associated with behavioral dysfunction in humans, such as mood disorders which include depression (e.g., Major Depressive Disorder), Bipolar Disorder, and Anxiety Disorder, and conditions characterized by atypical mood (e.g., depressed mood, irritability, instability of mood, and/or changes in mood), such as stress, hormonal mood swings (e.g., during pregnancy, during post-partum, during puberty, during menopause, or are a result of a Premenstrual Dysphoric Disorder or related condition), Mild Cognitive Impairment, substance-induced mood disorder (e.g., alcoholism), dementia, Alzheimer's disease, Parkinson's disease, Huntington's disease, and psychotic disorders (e.g., Schizoaffective Disorder, Schizophrenia, Delusional Disorder, and Psychotic Disorder Not Otherwise Specified).

Major Depressive Disorder (MDD) is a neuropsychiatric condition which afflicts anywhere from 10 to 20% of the population. In the United States, MDD is a contributing cause to the majority of the approximately 30,000 annual deaths by suicide. It has additionally been speculated that some unknown proportion of the 100,000 deaths by other unnatural means such as motor vehicle accidents, homicide and workplace accidents are also related to underlying depressive symptoms. Such deaths are the sixth leading cause of mortality in the United States. Medical treatment of depression over the years has included the use of psychotherapy and prescription anti-depressants. While generally helpful, these drugs are limited in their efficacy by their innate toxicity as well as a significant tendency to unpleasant side effects, such as nausea, sexual dysfunction, cognitive slowing, emotional dulling, lethargy, and sleep disturbances, as well as potentially dangerous interactions with other medications. Moreover, in some instances the subject being treated is a non-responder to the prescription anti-depressant therapy. More recently, an association has been noted between the use of modern (e.g., more conventional) prescription anti-depressants and the emergence of suicidal ideation, which is observed in a previously non-suicidal population. This risk appears particularly prominent in younger patients, e.g., those under the age of 24. This has in turn led to resistance to the use of this class of medication in pediatric, adolescent, and post-adolescent populations. Somewhat ironically, such under-treatment may have been associated with a spike in suicide deaths in the under-19 population between 2003 and 2004.

It therefore remains of great interest to explore safer alternatives for treating neuropsychiatric conditions, especially conditions associated with atypical mood, such as depression, e.g., Major Depressive Disorder.

SUMMARY

Nutrients and dietary supplements, sometimes referred to as "nutraceuticals," represent important alternatives or adjuncts to prescription anti-depressants. Recently, the first systematic (meta-analysis) review of nutraceuticals as adjuncts in the treatment of depression was conducted. See Sarris et al., *Am. J. Psychiatry* (2016) 173:575-587, the entire contents of which is incorporated herein by reference. From this comprehensive review of the clinical literature, it was concluded that SAMe, methyl folate, omega 3-fatty acids (specifically EPA) demonstrate particular promise as adjuncts in the treatment of depression and other diseases. Furthermore, this unique treatment option for depression and other diseases is described in U.S. Pat. No. 9,662,359, issued May 30, 2017 (corresponding to U.S. Publication No. 2013/0330429); and U.S. Pat. No. 8,372,451, issued Feb. 12, 2013 (corresponding to U.S. Publication No. 2011/0200690, published Aug. 18, 2011); the entire contents of each of which are incorporated herein by reference.

The present disclosure provides compositions, kits, and related methods, that incorporate a combination of therapeutics useful to treat, for example, neuropsychiatric conditions, such as depression. The combination of therapeutics described herein is expected to effectuate both anti-depressant and mood-stabilizing properties with little to no adverse side effects typically associated with prescription anti-depressants. The present disclosure also encompasses use of the therapy for the administration to subjects not necessarily diagnosed with a neuropsychiatric condition, such as subjects desiring wellness and/or energy; subjects having or likely to have coronary artery disease, liver disease, or osteoarthritis; pregnant subjects; and subjects having an abnormal folate metabolism due to a metabolic impairment preventing the absorption of neuroprotective nutrients. This therapy may be used therapeutically or prophylactically. In certain embodiments, the composition is designated by the Food and Drug Administration as a medical food.

In one aspect, provided is a composition comprising S-adenosyl methionine (SAMe), or a salt thereof, and a compound of Formula (I):

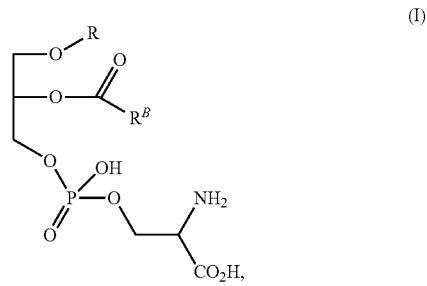

or a salt thereof, wherein R is hydrogen or $-C(=O)R^A$, wherein $R^A$ is unsubstituted $C_{10-18}$ alkykl; and $R^B$ is of the formula:

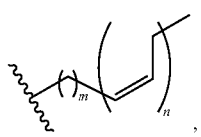

wherein m is 1, 2, 3, 4, 5, 6, or 7; and n is 1, 2, 3, 4, 5, 6, 7, or 8. In certain embodiments, the composition further comprises folic acid or a salt thereof or an active metabolite thereof (e.g., methyl folate or salt thereof). In certain embodiments, the composition further comprises one or more omega-3 fatty acids or salts thereof. In certain embodiments, the composition further comprises vitamin D3.

In another aspect, provided is a composition comprising folic acid, or a salt thereof, or an active metabolite thereof (e.g., methyl folate or salt thereof), and a compound of Formula (I):

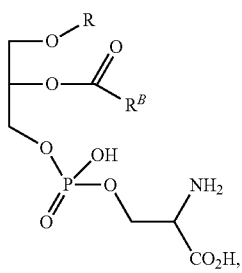
(I)

or a salt thereof, wherein R is hydrogen or —C(=O)$R^A$, wherein $R^A$ is unsubstituted $C_{10-18}$ alkyl; and $R^B$ is of the formula:

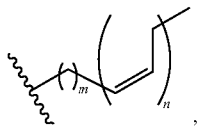

wherein m is 1, 2, 3, 4, 5, 6, or 7; and n is 1, 2, 3, 4, 5, 6, 7, or 8. In certain embodiments, the composition further comprises S-adenosyl methionine (SAMe) or salt thereof. In certain embodiments, the composition further comprises composition one or more omega-3 fatty acids or salts thereof. In certain embodiments, the composition further comprises vitamin D3.

In another aspect, provided is a composition comprising one or more omega-3 fatty acids, or salts thereof, and a compound of Formula (I):

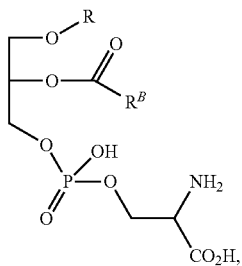
(I)

or a salt thereof, wherein R is hydrogen or —C(=O)$R^A$, wherein $R^A$ is unsubstituted $C_{10-18}$ alkyl; and $R_B$ is of the formula:

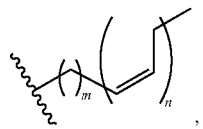

wherein m is 1, 2, 3, 4, 5, 6, or 7; and n is 1, 2, 3, 4, 5, 6, 7, or 8. In certain embodiments, the composition further comprises S-adenosyl methionine (SAMe) or salt thereof. In certain embodiments, the composition further comprises folic acid or a salt thereof or an active metabolite thereof (e.g., methyl folate or salt thereof). In certain embodiments, the composition further comprises vitamin D3.

In another aspect, provided is a composition comprising vitamin D3 and a compound of Formula (I):

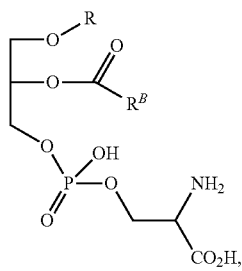
(I)

or a salt thereof, wherein R is hydrogen or —C(=O)$R^A$, wherein $R^A$ is unsubstituted $C_{10-18}$ alkyl; and $R^B$ is of the formula:

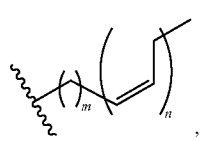

wherein m is 1, 2, 3, 4, 5, 6, or 7; and n is 1, 2, 3, 4, 5, 6, 7, or 8. In certain embodiments, the composition further comprises S-adenosyl methionine (SAMe) or salt thereof. In certain embodiments, the composition further comprises folic acid or a salt thereof or an active metabolite thereof (e.g., methyl folate or salt thereof). In certain embodiments, the composition further comprises one or more omega-3 fatty acids or salts thereof.

In another aspect, provided is a composition comprising a compound of Formula (I):

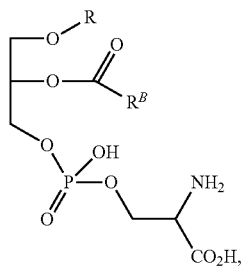
(I)

or a salt thereof, wherein R is hydrogen or —C(=O)R$^A$, wherein R$^A$ is unsubstituted C$_{10-18}$ alkyl; and R$^B$ is of the formula:

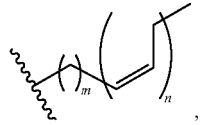

wherein m is 1, 2, 3, 4, 5, 6, or 7; and n is 1, 2, 3, 4, 5, 6, 7, or 8. In certain embodiments, the composition further comprises folic acid or a salt thereof or an active metabolite thereof (e.g., methyl folate or salt thereof). In certain embodiments, the composition further comprises S-adenosyl methionine (SAMe) or salt thereof. In certain embodiments, the composition further comprises one or more omega-3 fatty acids or salts thereof. In certain embodiments, the composition further comprises vitamin D3.

In certain embodiments, the composition comprises S-adenosyl methionine (SAMe), or a salt thereof; folic acid, or a salt thereof, or an active metabolite thereof (e.g., methyl folate or salt thereof); and a compound of Formula (I), or a salt thereof. In certain embodiments, the composition further comprises one or more omega-3 fatty acids, or salts thereof. In certain embodiments, the composition further comprises vitamin D3.

In certain embodiments, the composition consists essentially of S-adenosyl methionine (SAMe), or a salt thereof; folic acid, or a salt thereof, or an active metabolite thereof (e.g., methyl folate or salt thereof); and a compound of Formula (I), or a salt thereof. In certain embodiments, the composition consists essentially of S-adenosyl methionine (SAMe), or a salt thereof; folic acid, or a salt thereof, or an active metabolite thereof (e.g., methyl folate or salt thereof); a compound of Formula (I), or a salt thereof; and one or more omega-3 fatty acids, or salts thereof. In certain embodiments, the composition consists essentially of S-adenosyl methionine (SAMe), or a salt thereof; folic acid, or a salt thereof, or an active metabolite thereof (e.g., methyl folate or salt thereof); a compound of Formula (I), or a salt thereof; one or more omega-3 fatty acids, or salts thereof; and vitamin D3.

In certain embodiments, the one or more omega-3 fatty acids or salts thereof comprises at least 50% EPA.

In certain embodiments, the composition is formulated for oral administration.

In certain embodiments, S-adenosyl methionine, or a salt thereof, is provided in the composition in a range of between about 200 mg to about 2000 mg, inclusive, e.g., in a range of between about 800 mg to about 1600 mg, inclusive. In certain embodiments, folic acid, or a salt thereof, or an active metabolite thereof (e.g., methyl folate or salt thereof), is provided in the composition in a range of between about 1 mg to about 45 mg, inclusive, e.g., in a range of between about 5 mg to about 20 mg, inclusive. In certain embodiments, the compound of Formula (I), or salt thereof, is provided in the composition in a range of about 50 mg to about 1000 mg, inclusive; e.g., about 100 mg to about 500 mg, inclusive. In certain embodiments, one or more omega-3 fatty acids, or salts thereof, are provided in the composition in a range of between about 500 mg to about 5 g, inclusive, e.g., between about 800 mg to about 1600 mg, inclusive. In certain embodiments, vitamin D3 is provided in the composition in a range of between about 500 International Units (IU) to about 2000 International Units (IU), inclusive, e.g., between about 800 IU to about 1500 IU, inclusive; e.g., about 1000 IU.

Other components may be included in the composition. Such additional components may include, for example, prescription drugs, over-the-counter medicines, and/or vitamins. For example, in certain embodiments, the composition further comprises vitamin B$_{12}$. In certain embodiments, the vitamin B$_{12}$ is provided in the composition in a range of between about 100 μg to about 1000 μg, inclusive. In certain embodiments, the vitamin B$_{12}$ is provided in the composition in a range of between about 50 μg to about 500 μg, inclusive. In certain embodiments, the composition further comprises St. John's Wort (*Hypericum perforatum*). However, in certain embodiments, St. John's Wort is specifically excluded.

In certain embodiments, the composition further comprises a prescription anti-depressant. In certain embodiments, the compound is administered in combination with a prescription anti-depressant. In certain embodiments, the prescription anti-depressant is selected from the group consisting of selective serotonin reuptake inhibitors (SSRIs), serotonin and dopamine reuptake inhibitors (SDRIs), serotonin-norepinephrine reuptake inhibitors (SNRIs), serotonin-noradrenaline-dopamine reuptake inhibitors (SNDRIs), norepinephrine-dopamine reuptake inhibitors (NDRIs), norepinephrine (noradrenaline) reuptake inhibitors (NRIs), monoamine oxidase inhibitors (MAOIs), selective serotonin reuptake enhancers (SSREs), melatonergic agonists, tryptamines, tricyclic anti-depressants, and atypical anti-depressants.

In another aspect, provided is a method of treating a neuropsychiatric condition, the method comprising administering an effective amount of S-adenosyl methionine, or a salt thereof, and a compound of Formula (I):

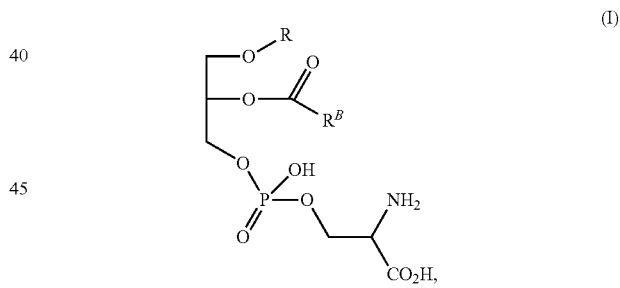

or a salt thereof, wherein R is hydrogen or —C(=O)R$^A$, wherein R$^A$ is unsubstituted C$_{10-18}$ alkyl; and R$^B$ is of the formula:

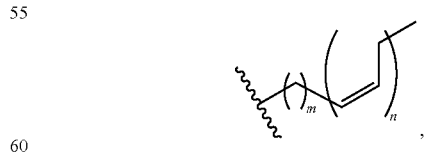

wherein m is 1, 2, 3, 4, 5, 6, or 7; and n is 1, 2, 3, 4, 5, 6, 7, or 8, to a subject in need thereof. In certain embodiments, the method further comprises administering folic acid, or a salt thereof, or an active metabolite thereof (e.g., methyl folate or salt thereof). In certain embodiments, the method further comprises administering one or more omega-3 fatty acids, or salts thereof. In certain embodiments, the method further comprises administering vitamin D3.

In another aspect, provided is a method of treating a neuropsychiatric condition, the method comprising administering an effective amount of folic acid, or a salt thereof, or an active metabolite thereof (e.g., methyl folate, or salt thereof), and a compound of Formula (I):

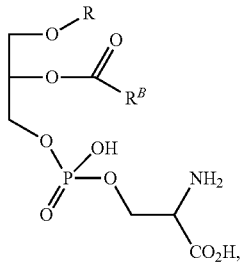
(I)

or a salt thereof, wherein R is hydrogen or —C(=O)R$^A$, wherein R$^A$ is unsubstituted C$_{10-18}$ alkyl; and R$^B$ is of the formula:

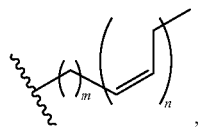

wherein m is 1, 2, 3, 4, 5, 6, or 7; and n is 1, 2, 3, 4, 5, 6, 7, or 8, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering vitamin D3.

In another aspect, provided is a method of treating a neuropsychiatric condition, the method comprising administering an effective amount of one or more omega-3 fatty acids, or salts thereof and a compound of Formula (I):

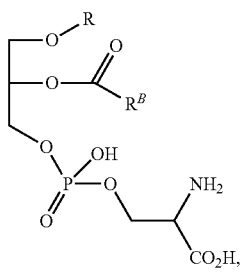
(I)

or a salt thereof, wherein R is hydrogen or —C(=)R$^A$, wherein R$^A$ is unsubstituted C$_{10-18}$ alkyl; and R$^B$ is of the formula:

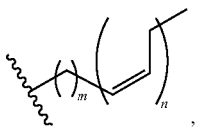

wherein m is 1, 2, 3, 4, 5, 6, or 7; and n is 1, 2, 3, 4, 5, 6, 7, or 8, to a subject in need thereof. In certain embodiments, the method further comprises administering S-adenosyl methionine, or a salt thereof. In certain embodiments, the method further comprises administering vitamin D3. In certain embodiments, the method further comprises administering folic acid, or a salt thereof, or an active metabolite thereof (e.g., methyl folate or salt thereof).

In another aspect, provided is a method of treating a neuropsychiatric condition, the method comprising administering an effective amount of vitamin D3 and a compound of Formula (I):

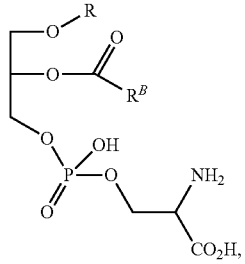
(I)

or a salt thereof, wherein R is hydrogen or —C(=O)R$^A$, wherein R$^A$ is unsubstituted C$_{10-18}$ alkyl; and R$^B$ is of the formula:

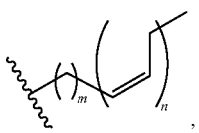

wherein m is 1, 2, 3, 4, 5, 6, or 7; and n is 1, 2, 3, 4, 5, 6, 7, or 8, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering folic acid, or a salt thereof, or an active metabolite thereof (e.g., methyl folate or salt thereof).

In another aspect, provided is a method of treating a neuropsychiatric condition, the method comprising administering an effective amount of a compound of Formula (I):

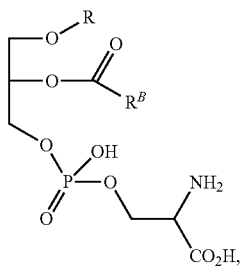

(I)

or a salt thereof, wherein R is hydrogen or —C(=O)R$^A$, wherein R$^A$ is unsubstituted C$_{10-18}$ alkyl; and R$^B$ is of the formula:

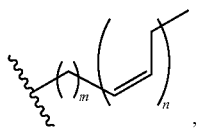

wherein m is 1, 2, 3, 4, 5, 6, or 7; and n is 1, 2, 3, 4, 5, 6, 7, or 8, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering folic acid, or a salt thereof, or an active metabolite thereof (e.g., methyl folate or salt thereof). In certain embodiments, the method further comprises administering vitamin D3. composition In certain embodiments, the neuropsychiatric condition is a mood disorder selected from the group consisting of depression, Bipolar Disorder, and Anxiety Disorder, or a condition characterized by atypical mood selected from the group consisting of stress, hormonal mood swings, Mild Cognitive Impairment, substance-induced mood disorders, dementia, Alzheimer's disease, Parkinson's disease, Huntington's disease, and psychotic disorders.

In certain embodiments, the hormonal mood swings take place during pregnancy, during post-partum, during puberty, during menopause, or are a result of a Premenstrual Dysphoric Disorder or related condition. In certain embodiments, the substance-induced mood disorder is a mood disorder induced by alcohol (e.g., alcoholism). In certain embodiments, the psychotic disorder is selected from the group consisting of Schizoaffective Disorder, Schizophrenia, Delusional Disorder, and Psychotic Disorder Not Otherwise Specified. In certain embodiments, depression is Major Depressive Disorder (MDD). In certain embodiments, the subject is not diagnosed with a Bipolar Disorder. In certain embodiments, the subject has not exhibited an episode of mania. In certain embodiments, the subject has or is at risk of having an Anxiety Disorder. In certain embodiments, the subject is a post-partum subject (e.g., a lactating post-partum subject).

In certain embodiments, the method comprises administering one or more of these therapeutic components, as described herein, in separate compositions. In certain embodiments, the subject is receiving or has received a prescription anti-depressant. In certain embodiments, the prescription anti-depressant is administered with the combination to the subject in an amount not effective to treat the disorder when administered alone. In certain embodiments, the prescription anti-depressant causes or is likely to cause an adverse side effect or undesired side effect in the subject. For example, in certain embodiments, the subject is at risk of suicide when administered an SSRI. In certain embodiments, the subject is a non-responder to a prescription anti-depressant.

In certain embodiments, the subject is a mammal, e.g., a domestic mammal or a human. In certain embodiments, the human subject is 24 years of age or younger. In certain embodiments, the human subject is between the age of 13 and 24. In certain embodiments, the human subject is between the age of 16 and 24.

In certain embodiments, the method further comprises the step of monitoring the effectiveness of the treatment in the subject.

Also provided is a kit comprising one or more of these therapeutic components, as described herein, a container, and instructions for use. In certain embodiments, the kit comprises a 7-day supply, 14-day supply, 30-day supply, 60-day supply, or 90-day supply of treatment.

The details of one or more embodiments of the disclosure are set forth in the Detailed Description of Certain Embodiments Section and the Examples as described below. Other features, objects, and advantages will be apparent from the description and from the claims.

DETAILED DESCRIPTION

The present disclosure is directed to compositions containing a specific combination of therapeutic components and methods of use thereof, wherein one or more of the therapeutic components provided in the combination is a complementary and alternative medicine (CAM) therapeutic. "Complementary and alternative medicine" (CAM) broadly refers to a non-conventional (e.g., non-prescription) drug-based therapies for effectuating improved health. Thus, CAM encompasses a group of diverse medical and health care systems, practices, and products that are not generally considered to be part of conventional medicine and includes a number of natural supplements. Complementary medicine is typically used together with standard medical care, while alternative medicine is typically used in place of standard medical care. The term CAM as used herein embraces both. In certain embodiments, the CAM therapeutic is designated by the Food and Drug Administration as a medical food.

The greater acceptance of non-prescription therapeutics by the traditional medical community, the perception of corporate bias in drug marketing, and a general tendency toward non-traditional and non-Western concepts of medical diagnosis and treatment have led to the development of CAM therapeutics, generally marketed and sold over-the-counter, as treatments for depression as well as other neuropsychiatric conditions, and in recent years, the market for CAM therapeutics has rivaled the size of the traditional medical marketplace. A neuropsychiatric condition, as used herein, is a condition associated with behavioral dysfunction in humans, such as atypical mood (e.g., depressed mood, irritability, instability of mood, and/or changes in mood). Exemplary neuropsychiatric conditions include, but are not limited to, depression (e.g., Major Depressive Disorder), Bipolar Disorder, and Anxiety Disorder, and conditions characterized by atypical mood, such as stress, hormonal mood swings (e.g., during pregnancy, post-partum, Premenstrual Dysphoric Disorder and related conditions, puberty, and menopause), Mild Cognitive Impairment, alcoholism, dementia, Alzheimer's disease, Parkinson's disease, Huntington's disease, and psychotic disorders (e.g., Schizoaffective Disorder, Schizophrenia, Delusional Disorder, and Psychotic Disorder Not Otherwise Specified). It is envisioned that the methods and compositions described herein will be effective for the treatment of a neuropsychiatric condition.

It is further contemplated that certain therapeutics described herein, e.g., SAMe, or a salt thereof; folic acid, or a salt thereof, or an active metabolite thereof; and a compound of Formula (I):

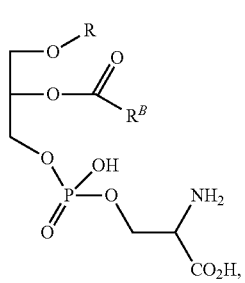

(I)

or a salt thereof, wherein R is hydrogen or —C(=O)R$^A$, wherein R$^A$ is unsubstituted C$_{10-18}$ alkyl; and R$^B$ is of the formula:

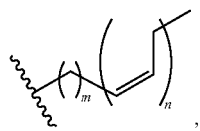

wherein m is 1, 2, 3, 4, 5, 6, or 7; and n is 1, 2, 3, 4, 5, 6, 7, or 8; and, optionally, one or more omega-3 fatty acids, or salts thereof; vitamin D3; and/or vitamin B$_{12}$, when combined is superior to other anti-depressant therapies. Furthermore, the combination of these therapeutic components, as described herein, is expected to cause significantly less (e.g., little, if any) side effects. For example, the combinations of therapeutic components described herein can be administered safely in treating a neuropsychiatric condition, such as depression, without the risk such as that associated with prescription anti-depressant-based therapies. Since one or more of the therapeutics used in the combination is commercially available and sold over-the-counter without a prescription (i.e., is a CAM therapeutic), the combination has the promise to be a widely accessible, safe, natural, and non-toxic alternative to prescription anti-depressants and mood stabilizers. This combination of agents may further be found useful in the treatment of subjects which may not have a neuropsychiatric condition, but would benefit from the therapy. For example, since the therapy described herein is deemed useful for the treatment of depressed mood, it is also envisioned this combination will be useful in the promotion of good health, energy, and/or happiness, in a subject (e.g., a "wellness energy booster"). Since there is a link between coronary artery disease and depression, it is also envisioned this combination will be useful in the treatment of coronary artery disease. Since there is a link between administration of SAMe and the treatment of liver disease and the treatment of pain associated with osteoarthritis, it is also envisioned this combination will be useful in the treatment of these diseases. Since folic acid and methyl folate have been found to be useful in the prevention of neural defects in an embryo or fetus, it is also envisioned this combination will be useful in the treatment of a pregnant or lactating post-partum subject.

S-Adenosyl Methionine

S-Adenosyl methionine (SAMe) is a naturally occurring substance in the human body and may also be referred to as S-adenosylmethionine, S-adenosyl-L-methionine, SAM-e®, or SAM herein. SAMe acts as a methyl donor in multiple metabolic processes. The methyl group (CH$_3$) attached to the methionine sulfur atom in SAMe is chemically reactive. This allows donation of this group to an acceptor substrate in transmethylation reactions.

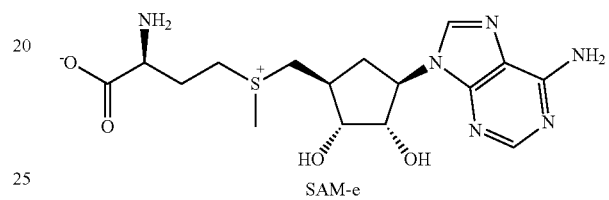

SAM-e

Another major role of SAMe is in polyamine biosynthesis. In particular, it is involved in the biosynthesis of several hormones and neurotransmitters that affect mood, such as dopamine and serotonin.

In the United States, SAMe is sold as an over-the-counter nutritional supplement. SAMe is also marketed under the brand names, GUMBARAL®, SAMYR®, ADOMET®, HEPTRAL® and ADMETHIONINE®, as a prescription drug approved in Russia, Italy, and Germany.

Some research, including multiple clinical trials, has indicated that taking SAMe on a regular basis may help treat or prevent depression (see, e.g., Kagan et al., *Am. J. Psychiatry* (1990) 147:591-595; Rosenbaum et al., *Acta Psychiatrica Scandinavica* (1990) 81:432-436). SAMe has been demonstrated in double-blind studies to be effective in the treatment of Major Depressive Disorder (MDD) when administered either intravenously or intramuscularly (parenterally). Two out of three double-blind studies of oral SAMe have shown efficacy when compared to placebo in the treatment of Major Depressive Disorder. A third study may have utilized an unstable form of the drug and did not demonstrate anti-depressant efficacy. SAMe has been shown to have some effectiveness for the treatment of liver disease (e.g., pruritus in cholestasis of pregnancy and intrahepatic cholestasis), and the pain of osteoarthritis (see *S-Adenosyl Methionine for Treatment of Depression, Osteoarthritis, and Liver Disease. Evidence Reports/Technology Assessments*, October 2002, No. 64). Generally, SAMe is well tolerated by most individuals.

Effective amounts of SAMe, or a salt thereof, range from about 200 mg to about 4000 mg per day for a human subject. In certain embodiments, about 200 mg to about 4000 mg of SAMe or a salt thereof per day is useful, e.g., about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 3000 mg or about 4000 mg, per day. In certain embodiments, SAMe or a salt thereof is provided in a range of between about 200 mg to about 4000 mg, between about 200 mg to about 2000 mg, between about 400 mg to about 2000 mg, between 400 mg to about 1000 mg, between about 500 mg to about 2000 mg, between about 600 mg to about 2000 mg, between about 700 mg to about 2000 mg, between about 800 mg to about 2000 mg, between about 800 mg to about 1600 mg, between about 800 to about 1500 mg, between about 800 mg to about 1400 mg, between about 800 mg to about 1300 mg, between about 800 mg to about 1200 mg, between about 800 mg to about 1100 mg, between about 800 mg to about 1000 mg, or between about 800 mg to about 900 mg, inclusive. In certain embodiments, the SAMe or a salt thereof is provided in a range of between about 800 mg to about 1600 mg. In certain embodiments, the amount of SAMe or a salt thereof administered per day is about 800 mg, about 1200 mg or about 1600 mg.

Oral SAMe achieves peak plasma concentrations 3 to 5 hours after ingestion of an enteric-coated tablet (e.g., containing between about 400 to about 1000 mg) (Najm et al., *BMC Musculoskelet. Disord.* (2004) 5:6). The half-life is about 100 minutes. It may require up to one month for it to reach full effectiveness in treating certain conditions. Because of structural instability, stable salt forms of SAMe are useful in oral compositions. Commonly used salts of SAMe include, without limitation, SAMe tosylate, SAMe butanedisulfonate, SAMe disulfate tosylate, SAMe disulfate ditosylate, and SAMe disulfate monotosylate salt. However, any salt form of SAMe may be employed in the therapeutic combination or method.

Folic Acid and Metabolites Thereof

Folic acid and its metabolite methylfolate are substances that are characterized as vitamins, essential nutrients available in small amounts in leafy vegetables and other foods. Folic acid (also known as vitamin $B_9$ or folacin) and folate (the naturally occurring form), as well as pteroyl-L-glutamic acid and pteroyl-L-glutamate, are forms of the water-soluble vitamin $B_9$. Folic acid is itself not biologically active, but its biological importance is due to tetrahydrofolate and other derivatives after its conversion to dihydrofolic acid in the liver.

All the biological functions of folic acid are performed by tetrahydrofolate and other derivatives. Their biological availability to the body depends upon dihydrofolate reductase action in the liver. This action is unusually slow in humans being less than 2% of that in rats. Moreover, in contrast to rats, an almost 5-fold variation in the activity of this enzyme exists between humans. Due to this low activity it has been suggested that this limits the conversion of folic acid into its biologically active forms when folic acid is consumed at levels higher than the Tolerable Upper Intake Level (about 1 mg per day for adults).

In the form of a series of tetrahydrofolate (THF) compounds, folate derivatives are substrates in a number of single-carbon-transfer reactions and also are involved in the synthesis of dTMP (2'-deoxythymidine-5'-phosphate) from dUMP (2'-deoxyuridine-5'-phosphate). It is a substrate for an important reaction that involves vitamin $B_{12}$. It is necessary for the synthesis of DNA and so is required for all dividing cells.

The pathway leading to the formation of methyl folate begins when folic acid (F), as folate, is reduced to dihydrofolate (DHF), which is then reduced to tetrahydrofolate (THF). The enzyme dihydrofolate reductase catalyses the last step. Vitamin $B_3$ in the form of NADPH is a necessary cofactor for both steps of the synthesis of DHF and THF.

Methylene-THF ($CH_2THF$) is formed from THF by the addition of methylene groups from one of three carbon donors: formaldehyde, serine, or glycine. Methyl folate ($CH_3$-THF) can be made from methylene-THF by reduction of the methylene group with NADPH. It is important to note that Vitamin $B_{12}$ is the only acceptor of methyl-THF. There is also only one acceptor for methyl-$B_{12}$ which is homocysteine in a reaction catalyzed by homocysteine methyltransferase. This is important because a defect in homocysteine methyltransferase or a deficiency of B12 can lead to a methyl-trap of THF and a subsequent deficiency. Thus, a deficiency in $B_{12}$ can generate a large pool of methyl-THF that is unable to undergo reactions and will mimic folate deficiency. Another form of THF, formyl-THF or folinic acid, results from oxidation of methylene-THF or is formed from formate donating a formyl group to THF. Finally, histidine can donate a single carbon to THF to form methenyl-THF.

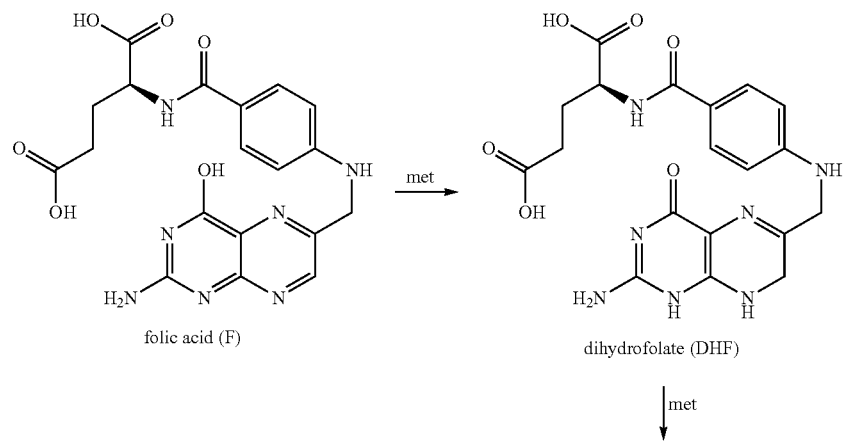

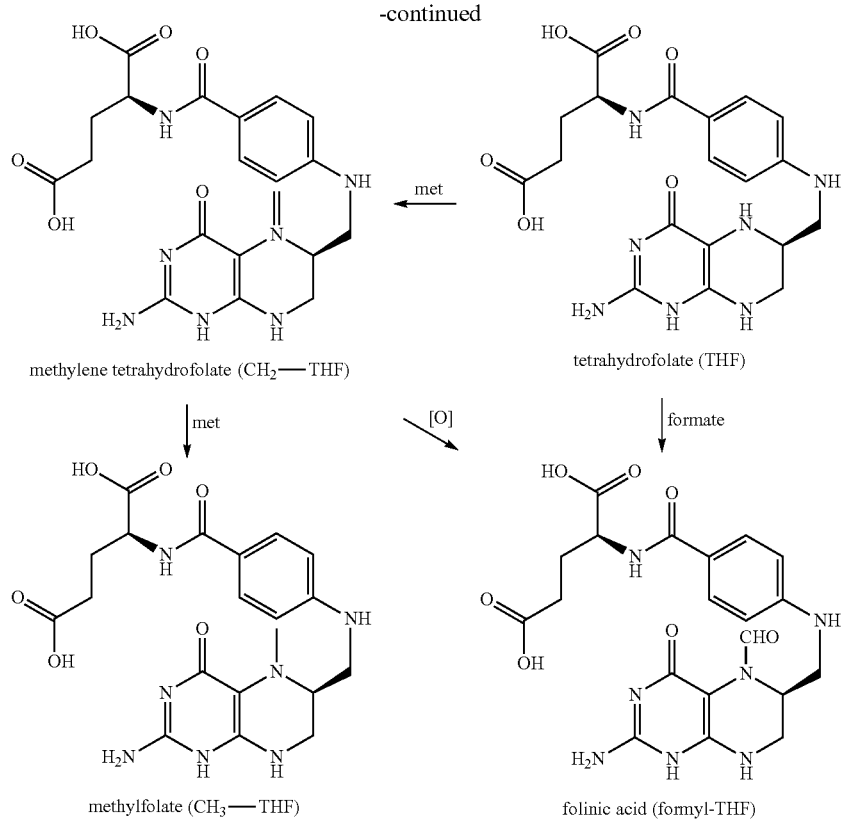

methylene tetrahydrofolate (CH₂—THF)

tetrahydrofolate (THF)

methylfolate (CH₃—THF)

folinic acid (formyl-THF)

Folic acid is available as an over-the-counter nutritional supplement and in prescription strength that has been used in the prevention of neural tube defects in the embryo or fetus of pregnant women. The use of folic acid or methyl folate has caused the near-elimination of the incidence of spina bifida, a devastating congenital birth defect. Thus, the present disclosure contemplates a method of preventive neural defects, such as spina bifida, in the embryo or fetus of a pregnant subject, comprising administering S-adenosyl methionine (SAMe), or a salt thereof; folic acid, or an active metabolite thereof, or a salt thereof; and a compound of Formula (I), or salt thereof, to the pregnant subject. The disclosure also contemplates a composition comprising these agents for the prevention of neural tube defects in the embryo or fetus of a pregnant subject.

Both folic acid and methyl folate are, like SAMe, methyl donors in multiple metabolic processes and have been studied as adjunctive therapy in Major Depressive Disorder. Low dose folic acid was found to be an effective augmenting strategy in female patients with an inadequate response to fluoxetine therapy, and a longer term study of folic acid supplementation in patients with both unipolar and bipolar depression showed statistically significant improvements in depression symptomatology. Strikingly, a recent study has demonstrated the efficacy of folic acid at higher dosages in the management of the manic phase of bipolar disorder, indicating possible efficacy as a mood stabilizer. Methyl folate has been helpful as primary treatment in patients suffering from comorbid depression and alcoholism. The related compound folinic acid (LEUCOVORIN®), a prescription drug utilized as an adjunct to chemotherapy agents, also showed a significant reduction in depression scores in patients who were inadequately responsive to monotherapy with a serotonin reuptake inhibitor.

Folic acid is well tolerated even at high dosages. The present disclosure contemplates effective amounts of folic acid or a salt thereof to be in a range of about 0.5 mg to about 5 mg, inclusive, per day for a human subject, e.g., about 0.5 mg, about 1 mg, about 1.5 mg, about 2 mg, about 2.5 mg or about 3 mg, per day. In certain embodiments, folic acid or a salt thereof is provided in a range of between about 1 mg to about 5 mg, between about 1 mg to about 4 mg, between 1 mg to about 3 mg, or between about 1 mg to about 2 mg, inclusive. In certain embodiments, folic acid or a salt thereof is provided in a range of between about 1 mg to about 3 mg.

A concern has been raised that extremely high doses of folic acid may be associated with a slightly higher risk of colorectal polyps or tumors, but this is controversial. There is also a concern that high doses of folic acid increases prostate cancer risk (Figueiredo et al., *J. National Cancer Institute* (2009) 101:432-435 Additionally, the use of folic acid without monitoring of serum $B_{12}$ levels may mask occult $B_{12}$ deficiency, which can be associated with irreversible neuro-cognitive changes.

In certain embodiments, methyl folate, also known as Me-THF, N5-Methyl-THF, MTHF, 5-MTHF, L-methylfolate, and Levomefolic acid, or a salt thereof is substituted for folic acid in the therapeutic combination, for example, as a way of enhancing efficacy and decreasing potential risks and complications (such as the theoretical tumor risk from the administration of the parent folic acid). Methyl folate calcium salt is available by prescription in the United States as Deplin® (L-methylfolate calcium salt). Methyl folate is also available as a medical food in the 7.5 mg to 45 mg dosage range. Methyl folate calcium salt is also available outside of the United States as Metafolin®, Bodyfolin®, and Nutrifolin®.

Moreover, a subject with an abnormal folate metabolism may benefit from the contemplated combination therapy. For example, individuals with 5-methyl tetrahydrofolate polymorphism, e.g., such as a C-to-T substitution at nucleotide 677 (677→T) mutation of the methylenetetrahydrofolate reductase (MTHFR) gene ("MTHFR 677C 4 T mutation") (See, e.g., Antoniades et al., *Circulation* (2009) 119:2507-2515), or an A-to-G substitution at nucleotide 2756 (2756A→G) mutation (See, e.g., Galbiatti et al., *Braz. J. Med. Biol. Res.* (2010) 43:445-450), may benefit from the administration of methyl folate or folinic acid rather than folic acid.

Effective amounts of methyl folate or a salt thereof range from about 1 mg to about 45 mg per day for a human subject. In certain embodiments, about 5 mg to about 45 mg of methyl folate or a salt thereof per day is useful, e.g., about 5 mg, about 7 mg, about 7.5 mg, about 10 mg, about 15 mg, about 20 mg, about 25 mg, about 30 mg, about 35 mg, about 40 mg, or about 45 mg, per day. In certain embodiments, methyl folate or a salt thereof is provided in a range of between about 5 mg to about 45 mg, between about 5 mg to about 40 mg, between 5 mg to about 35 mg, between about 5 mg to about 30 mg, between 5 mg to about 25 mg, between about 5 mg to about 20 mg, between about 5 mg to about 15 mg, between about 5 mg to about 10 mg, or between about 7 to about 15 mg, inclusive. In certain embodiments, methyl folate or a salt thereof is provided in a range of between about 5 mg to about 20 mg.

In certain embodiments, folinic acid or a salt thereof, such as LEUCOVORIN®, may be substituted for folic acid in the treatment. Effective amounts of folinic acid or a salt thereof range from about 5 mg to about 15 mg per day for a human subject. In certain embodiments, about 5 mg to about 15 mg of methyl folate or a salt thereof per day is useful, e.g., about 5 mg, about 6 mg, about 7 mg, about 8 mg, about 9 mg, about 10 mg, about 11 mg, about 12 mg, about 13 mg, about 14 mg, or about 15 mg, per day. In certain embodiments, methyl folate or a salt thereof is provided in a range of between about 5 mg to about 15 mg, between about 5 mg to about 10 mg, between about 5 mg to about 9 mg, between about 5 mg to about 8 mg, between about 5 mg to about 7 mg, or between about 5 mg to about 6 mg, inclusive.

Compounds of Formula (I)

Compounds of Formula (I) have the general structure:

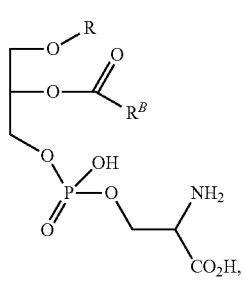

or a salt thereof, wherein:

R is hydrogen or —C(=O)R$^A$, wherein R$^A$ is unsubstituted $C_{10-18}$ alkyl; and R$^B$ is of the formula:

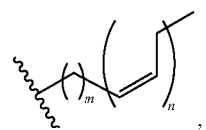

wherein wherein m is 1, 2, 3, 4, 5, 6, or 7; and n is 1, 2, 3, 4, 5, 6, 7, or 8.

As used herein, "alkyl" refers to a radical of a straight-chain or branched saturated hydrocarbon group having from 10 to 18 carbon atoms ("$C_{10-18}$ alkyl"). In some embodiments, an alkyl group has 10 to 17 carbon atoms ("$C_{10-17}$ alkyl"). In some embodiments, an alkyl group has 10 to 16 carbon atoms ("$C_{10-16}$ alkyl"). In some embodiments, an alkyl group has 10 to 15 carbon atoms ("$C_{10-15}$ alkyl"). In some embodiments, an alkyl group has 11 to 15 carbon atoms ("$C_{11-15}$ alkyl"). In some embodiments, an alkyl group has 12 to 15 carbon atoms ("$C_{12-15}$ alkyl"). In some embodiments, an alkyl group has 13 to 15 carbon atoms ("$C_{13-15}$ alkyl"). In some embodiments, an alkyl group has 14 to 15 carbon atoms ("$C_{14-15}$ alkyl"). In some embodiments, an alkyl group has 15 to 18 carbon atoms ("$C_{15-18}$ alkyl"). In some embodiments, an alkyl group has 13 carbon atoms ("$C_{13}$ alkyl"), 14 carbon atoms ("$C_{14}$ alkyl"), 15 carbon atoms ("$C_{15}$ alkyl"), or 16 carbon atoms ("$C_{16}$ alkyl").

In certain embodiments, the alkyl group is an n-alkyl group.

In certain embodiments, R is hydrogen. In certain embodiments, R is —C(=O)R$^A$.

In certain embodiments, R$^A$ is unsubstituted $C_{15-18}$ alkyl. In certain embodiments, R$^A$ is unsubstituted $C_{15}$ n-alkyl, i.e., R is

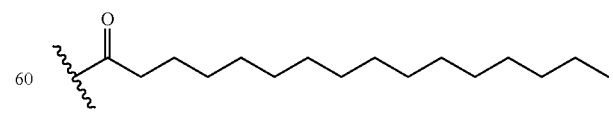

In certain embodiments, —C(=O)R$^B$ is an omega-3 fatty acid acyl moiety as provided in Table 1.

TABLE 1

| Common name of omega-3 fatty acid | Structure of —C(=)R$^B$ |
|---|---|
| α-Linolenic acid (ALA) | |
| Eicosapentaenoic acid (EPA) | |
| Docosapentaenoic acid (DPA), Clupanodonic acid | |
| Docosahexaenoic acid (DHA) | |

In certain embodiments, —C(=O)R$^B$ is of the formula:

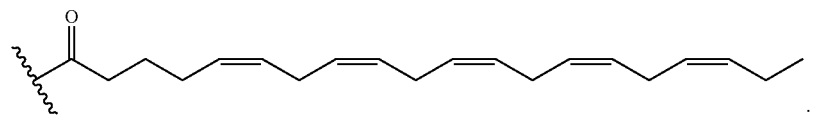 [SMILES: *C(=O)CCC/C=C\C/C=C\C/C=C\C/C=C\C/C=C\CC]

In certain embodiments, —C(=O)R$^B$ is of the formula:

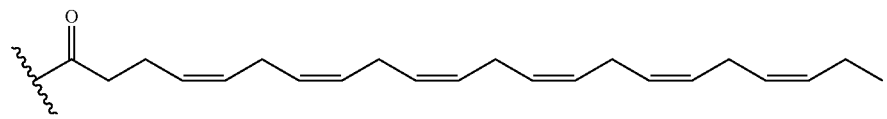

In certain embodiments, the compound of Formula (I) is of the formula:

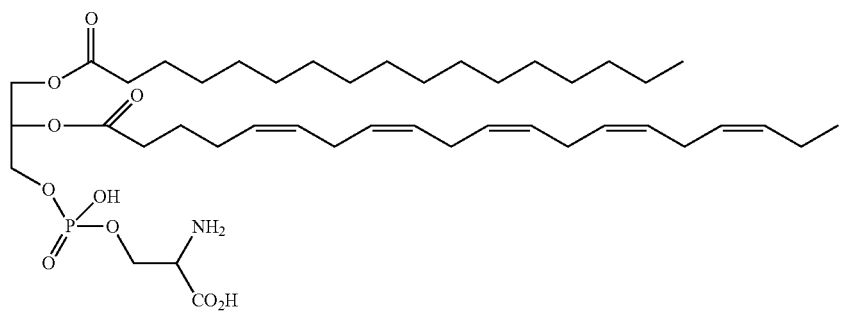 [SMILES: CC/C=C\C/C=C\C/C=C\C/C=C\C/C=C\CCCC(=O)OC(COC(=O)CCCCCCCCCCCCCCCC)COP(=O)(O)OCC(N)C(=O)O]

or a salt thereof, which is one of the active ingredients of Vayarin®.

In certain embodiments, the compound of Formula (I) is of the formula:

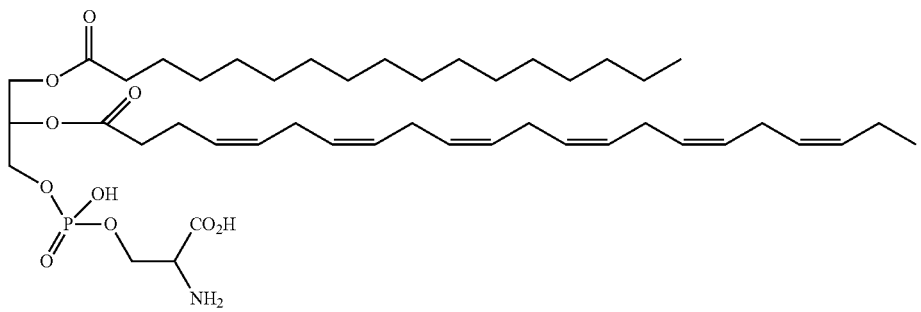 [SMILES: CC/C=C\C/C=C\C/C=C\C/C=C\C/C=C\C/C=C\CCC(=O)OC(COC(=O)CCCCCCCCCCCCCCCC)COP(=O)(O)OCC(N)C(=O)O]

or a salt thereof, which is one of the active ingredients of Vayacog®.

In certain embodiments, the compound of Formula (I), or salt thereof, is provided in the composition in a range of about 50 mg to about 1000 mg, inclusive; e.g., about 100 mg to about 500 mg, inclusive; about 100 mg to about 600 mg, inclusive; about 100 mg to about 700 mg, inclusive; about 100 mg to about 800 mg, inclusive; about 100 mg to about 900 mg, inclusive; about 50 mg to about 500 mg, inclusive; about 50 mg to about 400 mg, inclusive; about 50 mg to about 300 mg, inclusive; about 50 mg to about 200 mg, inclusive; or about 50 mg to about 100 mg, inclusive. In certain embodiments, the compound of Formula (I), or salt thereof, is provided in the composition in about 50 mg, 100 mg, 120 mg, 130 mg, 140 mg, 150 mg, 160 mg, 170 mg, 180 mg, 190 mg, or 200 mg.

Omega-3 Fatty Acids or Salts Thereof

Omega-3 fatty acids, or salts thereof, which may sometimes be referred to as n-3 fatty acids or ω-3 fatty acids, are a family of unsaturated fatty acids that have in common a final carbon-carbon double bond in the n-3 position; that is, the third bond from the methyl end of the fatty acid.

Omega-3 fatty acids or salts thereof include a-linolenic acid (18:3, n-3; ALA), eicosapentaenoic acid (20:5, n-3; EPA), and docosahexaenoic acid (22:6, n-3; DHA). These three polyunsaturates have either 3, 5 or 6 cis-double bonds in a carbon chain of 18, 20 or 22 carbon atoms, respectively. The human body cannot synthesize omega-3 fatty acids or salts thereof de novo, but it can form 20-carbon unsaturated omega-3 fatty acids or salts thereof (like EPA) and 22-carbon unsaturated omega-3 fatty acids or salts thereof (like DHA) from the eighteen-carbon omega-3 fatty acid α-linolenic acid. These conversions occur competitively with n-6 fatty acids, which are essential closely related chemical analogues that are derived from linoleic acid. Both the omega-3 α-linolenic acid and n-6 linoleic acid are essential nutrients which must be obtained from food sources.

Although omega-3 fatty acids or salts thereof have been known as essential to normal growth and health since the 1930s, awareness of their health benefits has dramatically increased in the past few years. New versions of ethyl esterized omega-3 fatty acids or salts thereof, such as E-EPA and combinations of E-EPA and E-DHA, have drawn attention as highly purified and more effective products than the traditional ones. In the United States, these novel versions are often sold as prescription medications, such as LOVAZA®. In the European Union, they are available as dietary supplements.

The health benefits of the long-chain omega-3 fatty acids or salts thereof, DHA and EPA omega-3, are the best known. These benefits were discovered in the 1970s by researchers studying the Greenland Inuit tribe. The Greenland Inuit people consume large amounts of fat from seafood but display virtually no cardiovascular disease. The high level of omega-3 fatty acids or salts thereof consumed by this population can reduce triglycerides, heart rate, blood pressure, and atherosclerosis.

Most naturally-produced fatty acids (created or transformed in animal or plant cells with an even number of carbon in chains) are in cis-configuration where they are more easily transformable. The trans-configuration results in much more stable chains that are very difficult to further breakdown or transform, forming longer chains that aggregate in tissues and lacking the necessary hydrophilic properties. This trans-configuration can be the result of the transformation in alkaline solutions or of the action of some bacteria that shorten the carbon chain. Natural transformations in plant or animal cells more rarely affect the last n-3 group itself. However, omega-3 compounds are still more fragile than n-6 because the last double bond is geometrically and electrically more exposed, notably in the natural cis configuration.

Table 2 provides different names for the most common omega-3 fatty acids or salts thereof found in nature.

TABLE 2

| Common name | Lipid name | Chemical name |
| --- | --- | --- |
| n/a | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |

TABLE 2-continued

| Common name | Lipid name | Chemical name |
|---|---|---|
| Tetracosapentaenoic acid | 24:5 (n-3) | all-cis-9,12,15,18,21-docosahexaenoic acid |
| Tetracosahexaenoic acid (nisinic acid) | 24:6 (n-3) | all-cis-6,9,12,15,18,21-tetracosenoic acid |

Omega-3 fatty acids, or salts thereof, have been suggested to have membrane-enhancing capabilities in brain cells. One medical explanation is that omega-3 fatty acids, or salts thereof, play a role in the fortification of the myelin sheaths around neurons.

A benefit of omega-3 fatty acids, or salts thereof, is believed to be, inter alia, helping the brain to repair damage by promoting neuronal growth. In a six-month study involving people with schizophrenia and Huntington's disease who were treated with E-EPA or a placebo, the placebo group had clearly lost cerebral tissue, while the patients given the supplements had a significant increase of grey and white matter.

In the prefrontal cortex (PFC) of the brain, low brain omega-3 fatty acids, or salts thereof, are thought to lower the dopaminergic neurotransmission in this brain area, possibly contributing to the negative and neurocognitive symptoms in schizophrenia. This reduction in dopamine system function in the PFC may lead to an overactivity in dopaminergic function in the limbic system of the brain which is suppressively controlled by the PFC dopamine system, causing the positive symptoms of schizophrenia. This is called the omega-3 polyunsaturated fatty acid/dopamine hypothesis of schizophrenia. This mechanism may explain why omega-3 supplementation shows effects against both positive, negative, and neurocognitive symptoms in schizophrenia.

Consequently, the past decade of omega-3 fatty acid research has led to some Western interest in omega-3 fatty acids, or salts thereof, as being a legitimate "brain food." A significant focus of research, however, lies in the role of omega-3 fatty acids, or salts thereof, as a non-prescription treatment for certain psychiatric and mental diagnoses and has become a topic of much research and speculation.

In a 1998, a small double-blind placebo-controlled study in thirty patients diagnosed with bipolar disorder was conducted. Most subjects in this study were already undergoing psychopharmacological treatment (e.g., 12 out of the 30 were taking lithium). Over the course of four months, 15 subjects were given capsules containing olive oil, and another 15 subjects were given capsules containing nine grams of pharmaceutical-quality EPA and DHA. The study showed that subjects in the omega-3 group were less likely to experience a relapse of symptoms in the four months of the study. Moreover, the omega-3 group experienced significantly more recovery than the placebo group.

Although the sample size of the study was too small to be clinically significant, additional lines of evidence subsequently emerged which appear to support the notion that omega-3 fatty acids, or salts thereof, may have beneficial effects on the psychiatric health of patients. For example, several epidemiological studies suggest co-variation between seafood consumption and rates of mood disorders. Biological marker studies indicate deficits in omega-3 fatty acids, or salts thereof, in people with depressive disorders, while several treatment studies indicate therapeutic benefits from omega-3 supplementation. A similar contribution of omega-3 fatty acids, or salts thereof, to the prevention of coronary artery disease may explain the well-described links between coronary artery disease and depression. Deficits in omega-3 fatty acids or salts thereof have been identified as a contributing factor to mood disorders and offer a potential rational treatment approach. Furthermore, a study conducted in 2004 found that 100 suicide attempt patients on average had significantly lower levels of EPA in their blood as compared to controls (Huan et al., *Biological psychiatry* (2004) 56: 490-6).

Based on these lines of evidence, in 2006 the Omega-3 fatty acids, or salts thereof, Subcommittee, assembled by the Committee on Research on Psychiatric Treatments of the American Psychiatric Association (APA) stated that the preponderance of epidemiologic and tissue compositional studies supports a protective effect of omega-3 fatty acid intake, particularly eicosapentaenoic acid (EPA) and docosahexaenoic acid (DHA), in mood disorders. Meta-analyses of randomized controlled trials demonstrate a statistically significant benefit in unipolar and bipolar depression ($p=0.02$). The results were highly heterogeneous, indicating that it is important to examine the characteristics of each individual study to note the differences in design and execution. EPA and DHA appear to have negligible risks and some potential benefit in major depressive disorder and bipolar disorder, but results remain inconclusive in most areas of interest in psychiatry. Health benefits of omega-3 EPA may be especially important in patients with neuropsychiatric conditions due to high prevalence rates of smoking and obesity and the metabolic side effects of some psychotropic medications.

Another meta-analysis published in the Journal of Clinical Psychiatry in 2007, based on 10 clinical trials, found that omega-3 polyunsaturated fatty acids significantly improved depression in patients with both unipolar and bipolar disorder. However, based upon the heterogeneity of the trials, the authors concluded that more large-scale, well-controlled trials were needed to find out the favorable target subjects, therapeutic dose of EPA and the composition of omega-3 PUFAs in treating depression. Additionally, a small American trial, published in 2009, suggests that E-EPA, as monotherapy, has an advantage over placebo in major depressive disorder (Mischoulon et al., *J Clin Psychiatry.* 2009 70:1636-1644). Conversely, a recent trial of DHA in a mood-disordered population had a negative result.

Omega-3 fatty acids, or salts thereof, in the form of fish oils are increasingly popular nutritional supplements which have shown efficacy as adjunctive therapy in the management of bipolar disorder, as well as in some studies of unipolar depressive illness. The mechanism of the omega-3 fatty acids, or salts thereof, in this population may involve a general neuroprotective effect, as well as possibly increased serotonergic or dopaminergic neurotransmission.

Thus, the methods and compositions described herein comprise one or more omega-3 fatty acids, or salts thereof, as part of a novel combination of therapeutics which acts synergistically and/or additively to treat a variety of conditions, such as a neuropsychiatric condition, e.g., depression.

It is further contemplated that about 500 mg to 5 grams of the one or more omega-3 fatty acids, or salts thereof, per day for a subject is suitable; e.g., about 500 mg, about 600 mg, about 700 mg, about 800 mg, about 900 mg, about 1000 mg, about 1200 mg, about 1400 mg, about 1600 mg, about 1800 mg, about 2 g, about 2.5 g, about 3 g, about 3.5 g, about 4 g, about 4.5 g, or about 5 g, per day. In certain embodiments, one or more omega-3 fatty acids or salts thereof is provided in a range of between about 500 mg to about 5 g, between about 500 mg to about 4 g, between 500 mg to about 3 g, between about 500 mg to about 2 g, between about 500 mg to about 1900 mg, between about 500 mg to about 1800 mg, between about 500 mg to about 1700 mg, between about 500 mg to about 1600 mg, between about 500 mg to about 1500 mg, between about 500 mg to about 1400 mg, between about 500 mg to about 1300 mg, between about 500 mg to about 1200 mg, between about 500 mg to about 1100 mg, between about 500 mg to about 1000 mg, between about 500 mg to about 900 mg, or between about 800 mg to about 1600 mg, inclusive. In certain embodiments, one or more omega-3 fatty acids, or salts thereof, is provided in a range of between about 800 mg to about 1600 mg.

In some embodiments, omega-3 fatty acids, or salts thereof, useful in the therapeutic combination are selected from E-EPA, EPA, DHA, or combinations thereof. In some embodiments, a higher proportion of EPA to other omega-3 fatty acids, or salts thereof, is used. For example, in certain embodiments, the one or more omega-3 fatty acids, or salts thereof, is rich in EPA or E-EPA, i.e., comprising at least about 50% EPA or E-EPA. In certain embodiments, the one or more omega-3 fatty acids, or salts thereof, comprise at least about 55%, at least about 60%, at least about 65%, at least about 70%, at least about 80%, at least about 90%, at least about 95%, of the one or more omega-3 fatty acids, or salts thereof, is EPA or E-EPA. In certain embodiments, the one or more omega-3 fatty acids, or salts thereof, is 100% EPA or E-EPA. In certain embodiments, the one or more omega-3 fatty acids, or salts thereof, comprise between about 50% to about 100% EPA or E-EPA, between about 55% to about 100% EPA or E-EPA, between about 60% to about 100% EPA or E-EPA, between about 65% to about 100% EPA or E-EPA, between about 70% to about 100% EPA or E-EPA, between about 75% to about 100% EPA or E-EPA, between about 80% to about 100% EPA or E-EPA, between about 85% to about 100% EPA or E-EPA, between about 90% to about 100% EPA or E-EPA, or between about 95% to about 100% EPA or E-EPA.

Omega-3 fatty acids, or salts thereof, are generally well tolerated, but they may result in mild gastrointestinal disturbances and fish taste in the subject's mouth. The supplements are believed to be non-toxic. The preponderance of formulations with different proportions of the primary omega-3 fatty acids, or salts thereof, EPA and DHA, as well as a concern about concentrated forms of the supplements possibly containing mercury from high fat fish such as tuna, are potential complications in using these substances in a large patient population.

Vitamins D3 and $B_{12}$

Vitamin D3, also known as cholecalciferol, is contemplated as an optional components of the therapeutic combination. In certain embodiments, vitamin D3 is provided in the composition in a range of between about 500 International Units (IU) to about 2000 International Units (IU), inclusive, e.g., between about 800 IU to about 1500 IU, inclusive; between about 500 IU to about 1200 IU, inclusive; between about 800 IU to about 1200 IU, inclusive; about 500 IU, 600 IU, 700 IU, 800 IU, 900 IU, 1000 IU, 1100 IU, 1200 IU, 1300 IU, 1400 IU, 1500 IU, 1600 IU, 1700 IU, 1800 IU, 1900 IU, or 2000 IU. In certain embodiments, vitamin D3 is provided in the composition in about 1000 IU.

Vitamin $B_{12}$, also called cobalamin, is also contemplated as an optional component of the therapeutic combination. Vitamin $B_{12}$ is a water soluble vitamin (formula: $C_{63}H_{88}CoN_{14}O_{14}P$) with a key role in the normal functioning of the brain and nervous system, and for the formation of blood. In certain embodiments, amounts of vitamin $B_{12}$ effective for treating a human subject with a neuropsychiatric condition, such as depression, is in a range of about 100 µg to about 2000 µg per day, e.g., about 100 µg, about 200 µg, about 300 µg, about 400 µg, about 500 µg, about 600 µg, about 700 µg, about 800 µg, about 900 µg, about 1000 µg, about 1500 µg, or about 2000 µg, per day. In certain embodiments, vitamin $B_{12}$ is provided in a range of between about 100 µg to about 2000 µg, between about 100 µg to about 1000 µg, between about 200 µg to about 1500 µg, between about 500 µg to about 1500 µg, between about 500 µg, to about 1000 µg, or between about 50 µg to about 500 µg, per day. In certain embodiments, vitamin $B_{12}$ is provided in a range of between about 50 µg to 500 µg, per day.

St. John's Wort

Additionally, St. John's Wort (*Hypericum perforatum*) has been extensively studied in treating depression, and while it appears to have efficacy in mild to moderate depressive illness in a number of controlled studies, conflicting results from meta-analyses have limited the willingness of physicians and other practitioners to prescribe this substance. A second consideration is that the substance is an herbal extract with multiple chemical constituents, some of which may interfere with the metabolism of prescribed medications.

St. John's Wort carries certain intrinsic limitations with respect to both the lack of robust evidence of efficacy in meta-analyses and its possible metabolic interactions with prescription drugs. In some embodiments described herein, the method and/or composition may further comprise St. John's Wort. In other embodiments, St. John's Wort is excluded in the methods and compositions contemplated herein.

Neuropsychiatric Conditions

As generally described above, the methods and compositions described herein are broadly effective for the treatment of neuropsychiatric conditions. Exemplary neuropsychiatric conditions that may be treated with the methods, compositions, and therapies include, but are not limited to, mood disorders or conditions characterized by atypical mood. A mood disorder is the term given for a group of diagnoses in the Diagnostic and *Statistical Manual of Mental Disorders* (DSM IV TR) classification system where a disturbance in the subject's mood is hypothesized to be the main underlying feature. The classification is known as mood (affective) disorders in ICD 10. Exemplary mood disorders include, but are not limited to depression (e.g., Major Depressive Disorder), Bipolar Disorder, and Anxiety Disorder. Exemplary conditions characterized by atypical mood (e.g., depressed mood, irritability, instability of mood, and/or changes in mood), include, but are not limited to, stress, hormonal mood swings (e.g., during pregnancy, postpartum, Premnstrual Dysphoric Disorder and related conditions, puberty, and menopause), Mild Cognitive Impairment, substance-induced mood disorders (e.g., alcoholism), dementia, Alzheimer's disease, Parkinson's disease, Huntington's disease, and psychotic disorders (e.g., Schizoaffective Disorder, Schizophrenia, Delusional Disorder, and Psychotic Disorder Not Otherwise Specified).

In certain embodiments, the neuropsychiatric condition is a condition characterized by atypical mood. In certain embodiments, the neuropsychiatric condition is selected from stress, hormonal mood swings, Mild Cognitive Impairment, substance-induced mood disorders, dementia, Alzheimer's disease, Parkinson's disease, Huntington's disease, and psychotic disorders.

In certain embodiments, the neuropsychiatric condition is hormonal mood swings, and the mood swings take place during pregnancy, post-partum, during puberty, or during menopause, or are a result of a Premenstrual Dysphoric Disorder or related condition. In certain embodiments, the subject is a post-partum subject.

In certain embodiments, the neuropsychiatric condition is substance-induced mood disorder, and the mood disorder is induced by alcohol (e.g., alcoholism).

In certain embodiments, the neuropsychiatric condition is a psychotic disorder selected from the group consisting of Schizoaffective Disorder, Schizophrenia, Delusional Disorder, and Psychotic Disorder Not Otherwise Specified.

In certain embodiments, the neuropsychiatric condition is a mood disorder. In certain embodiments, the mood disorder is Bipolar Disorder (e.g., the subject is a human subject who has been diagnosed with a Bipolar Disorder). In certain embodiments, the Bipolar Disorder is a depressed or mixed phase of Bipolar Disorder. In other embodiments, the subject is a human subject who is not diagnosed with a Bipolar Disorder. In some embodiments, the subject is a human subject who has not exhibited an episode of mania ("manic episode").

In certain embodiments, the mood disorder is anxiety (e.g., the subject is a human subject who has an Anxiety Disorder).

In certain embodiments, the mood disorder is depression. In certain embodiments, the depression is a Major Depressive Disorder (MDD). In certain embodiments, the depression is dysthymia (dysthymic disorder).

A major depressive episode is characterized by the presence of a severely depressed mood that generally persists for at least two weeks. Episodes may be isolated or recurrent and are categorized as mild (few symptoms in excess of minimum criteria), moderate, or severe (marked impact on social or occupational functioning). An episode with psychotic features, commonly referred to as psychotic depression, is automatically rated as severe. If the patient has had an episode of mania or markedly elevated mood, a diagnosis of bipolar disorder is made instead. Depression without mania is sometimes referred to as unipolar because the mood remains at one emotional state or "pole."

The most widely used criteria for diagnosing depressive conditions are found in the American Psychiatric Association's revised fourth edition of the *Diagnostic and Statistical Manual of Mental Disorders* (DSM-IV-TR), and the World Health Organization's *International Statistical Classification of Diseases and Related Health Problems* (ICD-10) which uses the name recurrent depressive disorder. The latter system is typically used in European countries, while the former is used in the United States and many other non-European nations, and the authors of both have worked towards conforming one with the other.

Major depressive disorder is classified as a mood disorder in DSM-IV-TR. The diagnosis hinges on the presence of a single or recurrent major depressive episode. Further qualifiers are used to classify both the episode itself and the course of the disorder. The category depressive disorder not otherwise specified is diagnosed if the depressive episode's manifestation does not meet the criteria for a major depressive episode. The ICD-10 system does not use the term major depressive disorder, but lists very similar criteria for the diagnosis of a depressive episode (mild, moderate, or severe); the term recurrent may be added if there have been multiple episodes without mania.

The DSM-IV-TR recognizes five further subtypes of MDD, called specifiers, in addition to noting the length, severity, and presence of psychotic features:

(1) Melancholic depression is characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss (not to be confused with anorexia nervosa), or excessive guilt.

(2) Atypical depression is characterized by mood reactivity (paradoxical anhedonia) and positivity, significant weight gain or increased appetite (comfort eating), excessive sleep or sleepiness (hypersomnia), a sensation of heaviness in limbs known as leaden paralysis, and significant social impairment as a consequence of hypersensitivity to perceived interpersonal rejection.

(3) Catatonic depression is a rare and severe form of major depression involving disturbances of motor behavior and other symptoms. Here the person is mute and almost stuporose, and either remains immobile or exhibits purposeless or even bizarre movements. Catatonic symptoms also occur in schizophrenia or in manic episodes, or may be caused by neuroleptic malignant syndrome.

(4) Postpartum depression (mild mental and behavioral disorders associated with the puerperium, not elsewhere classified in ICD-10) refers to the intense, sustained and sometimes disabling depression experienced by women after giving birth. Postpartum depression, which has incidence rate of 10-15% among new mothers, typically sets in within three months of labor, and lasts as long as three months.

(5) Seasonal affective disorder (SAD) is a form of depression in which depressive episodes come on in the autumn or winter, and resolve in spring. The diagnosis is made if at least two episodes have occurred in colder months with none at other times, over a two-year period or longer.

To confer major depressive disorder as the most likely diagnosis, other potential diagnoses must be considered, including dysthymia, adjustment disorder with depressed mood, and bipolar disorder. Dysthymia is a chronic, milder mood disturbance in which a person reports a low mood almost daily over a span of at least two years. The symptoms are not as severe as those for major depression, although people with dysthymia are vulnerable to secondary episodes of major depression (sometimes referred to as double depression). Adjustment disorder with depressed mood is a mood disturbance appearing as a psychological response to an identifiable event or stressor, in which the resulting emotional or behavioral symptoms are significant but do not meet the criteria for a major depressive episode. Bipolar disorder, previously known as manic-depressive disorder, is a condition in which depressive phases alternate with periods of mania or hypomania. Although depression is currently categorized as a separate disorder, there is ongoing debate because individuals diagnosed with major depression often experience some hypomanic symptoms, indicating a mood disorder continuum.

The criteria have been criticized because they do not take into account any other aspects of the personal and social context in which depression can occur. In addition, some studies have found little empirical support for the DSM-IV cut-off criteria, indicating they are a diagnostic convention imposed on a continuum of depressive symptoms of varying severity and duration: excluded are a range of related diagnoses, including dysthymia which involves a chronic but milder mood disturbance, recurrent brief depression which involves briefer depressive episodes, minor depressive disorder which involves only some of the symptoms of major depression, and adjustment disorder with depressed mood which involves low mood resulting from a psychological response to an identifiable event or stressor.

There are significant practical implications for the diagnosis or misdiagnosis of MDD versus other related but distinct disorders in regards to prescription anti-depressant-based therapies because these conditions are generally treated with different sets of medications. For example, widely used anti-depressants such as SSRIs, which are prescribed to patients diagnosed with MDD, may cause adverse effects with potentially severe clinical consequences, or, conversely, may show lack of efficacy when unknowingly prescribed to patients with bipolar disorder, which is, unfortunately, a fairly common clinical scenario. By contrast, these risks can be circumvented by using the compositions and methods described herein. The therapy contemplated provides a safe and effective alternative for treating conditions that broadly include mood disorders, ranging from mild mood disturbances such as dysthymia to severe forms of depression such as MDD. Therefore, for those manifesting certain symptoms of a mood disorder but where diagnosis of MDD is as yet ambiguous and therefore may not meet the clinical criteria appropriate for treatment with a prescription anti-depressant-based drug therapy, the therapy can still be safely administered.

Symptoms of Depression

Subjects who may benefit from the therapy described herein can be identified by practitioners using routine evaluations. The challenge facing clinicians striving for an accurate diagnosis of these conditions stems in part from the fact that there are a number of overlapping symptoms across these conditions. Many of these symptoms, which are described in more detail below, can be remedied or alleviated when the therapy is used according to this disclosure.

A person suffering a major depressive episode usually exhibits a very low mood, which pervades all aspects of life, and an inability to experience pleasure in activities that formerly were enjoyed. Depressed people may be preoccupied with, or ruminate over, thoughts and feelings of worthlessness, inappropriate guilt or regret, helplessness, hopelessness, and self-hatred. In severe cases, depressed people may have symptoms of psychosis. These symptoms include delusions or, less commonly, hallucinations, usually of an unpleasant nature. Other symptoms of depression include poor concentration and memory (especially in those with melancholic or psychotic features), withdrawal from social situations and activities, reduced sex drive, and thoughts of death or suicide.

Insomnia is common in the depressed population. In the typical pattern, a person wakes very early and is unable to get back to sleep. Hypersomnia, or oversleeping, is less common. Appetite often decreases, with resulting weight loss, although increased appetite and weight gain occasionally occur. The person may report multiple physical symptoms such as fatigue, headaches, or digestive problems; physical complaints are the most common presenting problem in developing countries, according to the World Health Organization's criteria for depression. Family and friends may notice that the person's behavior is either agitated or lethargic.

Depressed children often display an irritable rather than a depressed mood, and show varying symptoms depending on age and situation. Most exhibit a loss of interest in school and a decline in academic performance. They may be described as clingy, demanding, dependent, or insecure. Diagnosis may be delayed or missed when symptoms are interpreted as normal moodiness. Depression may also coincide with attention-deficit hyperactivity disorder (ADHD), complicating the diagnosis and treatment of both.

High risks associated with misdiagnosis and misuse of a prescription anti-depressant are markedly reduced for the therapy. For instance, for a population of subjects who may be categorized near "borderline" for the diagnosis of MDD and therefore may not receive a prescription anti-depressant due to inherent risks may still be safely administered a therapy described herein.

Diagnosis and Clinical Assessment

Generally, a diagnostic assessment requires that it be conducted by a general practitioner, or by a psychiatrist or psychologist, who records the person's current circumstances, biographical history, and current symptoms, and a family medical history to see if other family members have suffered from a mood disorder, and discusses the person's alcohol and drug use. The assessment also includes a mental state examination, which is an assessment of the person's current mood and thought content, in particular the presence of themes of hopelessness or pessimism, self-harm or suicide, and an absence of positive thoughts or plans. Specialist mental health services are rare in rural areas, and thus diagnosis and management is largely left to primary care clinicians. This issue is even more marked in developing countries. The score on a rating scale alone is not sufficient to diagnose depression, but it provides an indication of the severity of symptoms for a time period, so a person who scores above a given cut-off point can be more thoroughly evaluated for a depressive disorder diagnosis. Several rating scales are used for this purpose. Screening programs have been advocated to improve detection of depression, but there is evidence that they do not improve detection rates, treatment, or outcome.

Primary care physicians and other non-psychiatrist physicians have difficulty diagnosing depression. In light of the fact that non-psychiatrists miss two-thirds of cases and unnecessarily treat other patients, these patients who fall within the "gray area" of diagnosis of related psychiatric disorders may greatly benefit from the therapy described herein.

Before diagnosing a mood disorder, such as major depressive disorder, a doctor generally performs a medical examination and selected investigations to rule out other causes of symptoms. These include blood tests measuring TSH and thyroxine to exclude hypothyroidism; basic electrolytes and serum calcium to rule out a metabolic disturbance; and a full blood count including ESR to rule out a systemic infection or chronic disease. Adverse affective reactions to medications or alcohol misuse are often ruled out, as well. Testosterone levels may be evaluated to diagnose hypogonadism, associated with depression in men. The step of eliminating other potential causes such as these, which are usually traced to physical or mechanical bases, as opposed to psychiatric or biochemical, should be performed for accurate diagnosis of a mood disorder.

Subjective cognitive complaints appear in older depressed people, but they can also be indicative of the onset of a dementing disorder, such as Alzheimer's disease. Depression is also a common initial symptom of dementia. The challenge includes the fact that no biological tests confirm major depression. For prescribing a prescription anti-depressant such as an SSRI, therefore, cognitive testing and brain imaging are generally used to help distinguish depression from dementia. A CT scan or MRI exam may also be used to exclude brain pathology in those with psychotic, rapid-onset or otherwise unusual symptoms before a prescription anti-depressant may be prescribed to the patient. The process is time-consuming, expensive and accompanies risks of misdiagnosis and improper use of anti-depressant drugs. These problems may be greatly eliminated by using instead the compositions and methods described herein. The therapy described here is believed to be also effective for treating depression that is associated with dementia. It is understood by one of ordinary skill in the art that such therapy may be administered in conjunction with additional therapeutic directed to treat the underlying pathology, such as dementia and/or Alzheimer's disease.

In some embodiments, similarly, the therapy is also useful for treating mood disorders associated with or induced by substance abuse (e.g., alcohol or drug consumption). Without being bound by any particular theory, it is believed that the particular combinations of therapeutics described herein can synergistically act as a general mood stabilizer. As such, the combination of therapeutics contemplated herein can be used to treat mood disturbances triggered by extrinsic and/or behavioral attributes such as substance abuse without the risks that prescription anti-depressants may pose.

Surprisingly, the combination of therapeutics described herein may also be effective as a mood-stabilizer or anxiolytic. Therefore, the treatment protocol and/or composition may also be useful for the treatment of the depressed or mixed phase of bipolar disorders, anxiety disorders, and related conditions such as atypical mood disorders, in which subjects would benefit from stabilizing or neutralizing moods. This may be particularly useful for subjects who experience or are likely to experience adverse side effects from prescription anti-depressant therapies, which are known to cause certain degree of irritability in patients. Some of these side effects associated with prescription anti-depressants are described in more detail herein.

Thus, the therapy does not present many of the issues and risks associated with prescription anti-depressant-based therapies (e.g., delayed or inaccurate diagnosis, misdiagnosis, misuse of anti-depressants, inherent risks associated with the drugs that require caution, significant side effects which may lead to noncompliance, especially sexual side effects, and possibly emergent suicidality associated with anti-depressant treatment of pediatric populations) and therefore can be used more liberally and safely, and as effectively, as compared to a typical SSRI-based therapy for treating a broad spectrum of mood disorders. Again, the therapy causes little, if any, side effects and adverse drug interactions even when used together with other therapeutics.

Thus, in any of the above embodiments, the method may further comprise the step of identifying a subject having or at risk of developing a MDD.

In any of the above embodiments, the method of treatment may further comprise the step of monitoring the effectiveness of the treatment in the subject over a period of time.

Prescription Anti-Depressant Therapies and Side Effects

As mentioned, the therapy offers much advantage over prescription anti-depressants and may be substituted partially or entirely for the treatment of a neuropsychiatric condition, such as depression.

However, it may be useful to also administer together or separately a prescription anti-depressant with the therapy. Various types (e.g., classes) of anti-depressants are known and commercially available and are in some cases referred to as "conventional" anti-depressants. Any subjects who take one or more of these anti-depressants may therefore be good candidates for receiving the therapy.

Thus, in some embodiments, the method involves a combination therapy comprising administering the therapy together with one or more prescription anti-depressants. In certain embodiments, the prescription anti-depressant therapy is administered to the subject in an amount not effective to treat the condition when administered alone.

Prescription anti-depressants include, but are not limited to: selective serotonin reuptake inhibitors (SSRIs), serotonin and dopamine reuptake inhibitors (SDRIs), serotonin-norepinephrine reuptake inhibitors (SNRIs), serotonin-noradrenaline-dopamine reuptake inhibitors (SNDRIs), norepinephrine-dopamine reuptake inhibitors (NDRIs), norepinephrine (noradrenaline) reuptake inhibitors (NRIs), monoamine oxidase inhibitors (MAOIs), selective serotonin reuptake enhancers (SSREs), melatonergic agonists, tryptamines, tricyclic anti-depressants, and atypical anti-depressants.

SSRIs are said to work by preventing the reuptake of serotonin (5-HT) by the presynaptic neuron, thus maintaining higher levels of 5-HT in the synapse. Examples of SSRIs include but are not limited to the following (trade names in parentheses): alaproclate; amoxapine; citalopram (such as CELEXA®, CIPRAMIL®, EMOCAL®, SEPRAM® and SEROPRAM®); clomipramine; dapoxetine; duloxetine (such as CYMBALTA®); escitalopram oxalate (such as LEXAPRO®, CIPRALEX® and ESERTIA®); femoxetine; fenfluramine; fluoxetine (such as PROZAC®, FONTEX®, SEROMEX®, SERONIL®, SARAFEM®, FLUCTIN® (EUR), and FLUOX® (NZ)); fluvoxamine maleate (such as LUVOX®, FAVERIN®, and DUMYROX®); indalpine; milnacipran; norfenfluramine; olanzapine; paroxetine (such as PAXIL®, SEROXAT®, AROPAX®, DEROXAT®, REXETIN®, XETANOR®, and PAROXAT®); sertraline (such as ZOLOFT®, LUSTRAL® and SERLAIN®); trazodone (such as DESYREL®, MOLIPAXIN®, TRITTICO®, THOMBRAN®, TRIALODINE®, TRAZOREL®, TRITICUM®, and TRAZONE®); venlafaxine and zimelidine.

Bupropion, sold as WELLBUTRIN®, is a non-limiting example of a serotonin and dopamine reuptake inhibitor (SDRI).

Non-limiting examples of SNRIs include: venlafaxine (EFFEXOR XR®, EFFEXOR®); desvenlafaxine (PRISTIQ®) available from Wyeth; sibutramine (MERIDIA®, REDUCTIL®); nefazodone (SERZONE®); milnacipran (DALCIPRAN®/Portugal; IXEL®/France); duloxetine (CYMBALTA®) available from Eli Lilly and Company; and, bicifadine available from DOV Pharmaceutical.

SNDRIs are the serotonin-noradrenaline-dopamine reuptake inhibitors. Non-limiting examples of SNDRIs include: tesofensine, brasofensine; and GlaxoSmithKline's NS2359; Nomifensine; Venlafaxine (EFFEXOR®) and Sibutramine (MERIDIA®/REDUCTIL®).

Norepinephrine-dopamine reuptake inhibitors (NDRI) such as bupropion (WELLBUTRIN®, ZYBAN®) inhibit the neuronal reuptake of dopamine and norepinephrine (noradrenaline).

Noradrenergic and specific serotonergic anti-depressants (NASSAs) form a newer class of anti-depressants which purportedly work to increase norepinephrine (noradrenaline) and serotonin neurotransmission by blocking presynaptic alpha-2 adrenergic receptors while at the same time minimizing serotonin related side-effects by blocking certain serotonin receptors. The only example of this class in clinical use is mirtazapine (AVANZA®, ZISPIN®, REMERON®).

Norepinephrine (noradrenaline) reuptake inhibitors (NRIs) such as reboxetine (EDRONAX®) act via norepinephrine (also known as noradrenaline). NRIs are thought to have a positive effect on concentration and motivation in particular. These include, without limitation, atomoxetine, maprotiline, nisoxetine, reboxetine, viloxazine and TCAs/Tetras (such as AMITRIPTYLINE®, AMOXAPINE®, BUTRIPTYLINE®, DESIPRAMINE®/LOFEPRAMINE®, DIBENZEPIN®, DOSULEPIN®, DOXEPIN®, IMIPRAMINE®, IPRINDOLE®, MELITRACEN®, NORTRIPTYLINE®, OPIPRAMOL®, PROTRIPTYLINE®, TRIMIPRAMINE®, and MAPROTILINE®).

Monoamine oxidase inhibitors (MAOIs) are a class of powerful anti-depressant drugs that act by inhibiting the activity of monoamine oxidase preventing the breakdown of monoamine neurotransmitters, which increases their availability. There are two isoforms of monoamine oxidase, MAO-A and MAO-B. Non-limiting examples of MAOIs include: iproclozide, iproniazid, isocarboxazid, nialamide, pargyline, phenelzine, rasagiline, selegiline, toloxatone, tranylcypromine, RIMAs (brofaromine, beta-carbolines (harmaline) and moclobemide).

Selective serotonin reuptake enhancers (SSREs) are antidepressants that enhance the reuptake of serotonin instead of inhibiting it, as tricyclic anti-depressants and selective serotonin reuptake inhibitors (SSRIs) do. One known selective serotonin reuptake enhancer is tianeptine (INN) (available under the tradenames: STABLON®, COAXIL®, and TATINOL®).

Furthermore, tricyclic anti-depressants (TCAs) work on both serotonin and norepinephrine transporters. This class includes desipramine, which is sold under the trade names of NORPRAMIN® and PERTOFRANEIS®.

Another class of anti-depressant more recently made available includes a melatonergic anti-depressant, such as VALDOXAN® (agomelatine).

Problems associated with these therapeutic regimen include adverse or unwanted side effects and lack of responsiveness in certain sub-population of affected individuals. Therefore, the therapeutic methods and compositions described herein are particularly suitable for subjects who either experience unwanted side effects from prescription anti-depressant therapies or at risk of developing adverse effects, as well as those who do not benefit from the conventional approach.

For example, in some cases, a patient suffering from MDD is classified to be a "non-responder." The term "non-responder" refers to a subject who is resistant to a particular therapy, e.g., agent or drug such as an SSRI-based therapy. Thus, in some cases, a non-responder patient is unresponsive or substantially unresponsive to SSRI treatment. As used herein, "unresponsive or substantially unresponsive to SSRI treatment" means that the patient does not significantly improve symptoms and/or severity of the disorder in response to the SSRI treatment. Evaluation of patients in assessing symptoms and/or severity of the disorder may be carried out by various methods, which are known in the art. The evaluation may take into account numerous criteria, as determined by suitable biochemical, physiological and/or behavioral factors.

Some patients experience adverse or undesired side effects from a convention drug therapy. The most widely prescribed anti-depressants come from a class of medications known as selective serotonin reuptake inhibitors (SSRIs). Examples of SSRIs include, but are not limited to, fluoxetine (PROZAC®), fluvoxamine (LUVOX®), sertraline (ZOLOFT®), paroxetine (PAXIL®), escitalopram (LEXAPRO®), and citalopram (CELEXA®). The SSRIs act on serotonin in the brain. Serotonin plays a role in the regulation of mood, digestion, pain, sleep, mental clarity, and other biological functions. As a result, the SSRI anti-depressants can cause a wide range of side effects. Some side effects of SSRI anti-depressants include, but are not limited to, nausea, insomnia, anxiety, restlessness, decreased sex drive, dizziness, weight gain or loss, tremors, sweating, sleepiness, fatigue, dry mouth, diarrhea, constipation and headaches. Common side effects include sexual problems including delayed orgasm or anorgasmia in both sexes, erectile dysfunction in men, drowsiness, sleep difficulties, and nausea. While some side effects subside after the first few weeks of drug treatment, others persist and may even get worse. In pediatric and young adult populations up till the age of 24, the SSRIs have been associated with the emergence of suicidal ideation and behavior. In addition, for older patients (e.g., 65 or older), SSRIs may pose an additional concern. Studies have shown that SSRI medications may increase the risk for falls, fractures, and bone loss in older adults. The SSRIs can also cause serious withdrawal symptoms when discontinued abruptly.

There are a variety of newer anti-depressant drugs, termed atypical anti-depressants, which target other neurotransmitters either alone or in addition to serotonin. Some of the brain chemicals they affect include norepinephrine and dopamine.

The atypical anti-depressants include, but are not limited to: bupropion (WELLBUTRIN®), mirtazapine (REMERON®), venlafaxine (EFFEXOR®), duloxetine (CYMBALTA®), trazodone (DESYREL®), and nefazodone (formerly available as SERZONE®). The side effects vary according to the specific drug. However, many of the atypical anti-depressants can cause nausea, fatigue, weight gain, sleepiness, nervousness, dry mouth, and blurred vision.

Side effects of older anti-depressant drugs are generally more severe than those of the newer drugs. As such, they are usually only prescribed as a last resort after other treatments and medications have failed. For example, tricyclic anti-depressants and MAOIs (monoamine oxidase inhibitors) are older classes of anti-depressants. People taking MAOIs need to be careful about the foods they eat and the medicines they take. For example, the tricyclic drugs are cardiotoxic and potentially fatal when taken in overdose. Foods and medicines that contain high levels of a chemical called tyramine are dangerous for people taking MAOIs. Tyramine is found in some cheeses, wines, and pickles. The chemical is also in some medications, including decongestants and over-the-counter cold medicine. Mixing MAOIs and tyramine can cause a sharp increase in blood pressure, which can lead to stroke. The combined use of MAOIs and meperidine (DE-MEROL®) or any SSRI compound can result in death.

In addition, prescription anti-depressant therapies such as those provided above may cause significant withdrawal symptoms upon termination of the therapy. Patients may experience a number of unpleasant withdrawal symptoms such as crying spells, extreme restlessness, dizziness, fatigue, and aches and pains. These withdrawal symptoms are known as anti-depressant discontinuation syndrome. Anti-depressant discontinuation syndrome is especially associated with taking PAXIL® or EFFEXOR®. However, any conventional medications for depression can cause withdrawal symptoms. Anti-depressant withdrawal symptoms may include the following: anxiety, agitation, depression, mood swings, flu-like symptoms, irritability and aggression, insomnia, nightmares, nausea and vomiting, dizziness, loss of coordination, stomach cramping and pain, electric shock sensations, tremor and muscle spasms. Depression and anxiety are also common symptoms when withdrawing from anti-depressants. When depression is a withdrawal symptom, it's often worse than the original depression that led to drug treatment in the first place. Unfortunately, many people mistake this withdrawal symptom for a return of their depressive illness and resume medication, creating a vicious circle.

Thus, to avoid the risk of developing adverse effects associated with prescription anti-depressant therapies, it is desirable to reduce the amount (e.g., dose) of a prescription anti-depressant necessary to effectively treat depression, or preferably replace it altogether or at least partially with an alternative, which does not cause these adverse effects. Indeed, the compositions and treatment protocols comprising a combination of therapeutics provides an effective and safe alternative. Furthermore, the compositions and treatment protocols described herein, when used in conjunction with one or more prescription anti-depressant therapies, may allow patients to reduce the amount of the prescription anti-depressant needed to maintain the effectiveness of the treatment, thereby reducing or minimizing unwanted side effects associated with the drug. In some cases, the patients may completely replace the conventional therapy with an combination therapy without compromising the overall efficacy of the treatment of depression. This expectation is based on the notion that when the composition or the method provided herein is used in conjunction with a conventional therapy it may be possible to reduce the amount of the medicament to a dose that by itself is ineffective in treating depression, thereby replacing entirely or partially a dosage of the medicament. This is particularly useful to avoid or reduce unwanted side effects from the drug (medicament), e.g., SSRIs, when an effective amount of the drug accompanies adverse effects in the subject. For example, when used in combination with the method described herein, an effective dose for a conventional therapeutic agent may be reduced by 10%, 20%, 30%, 40%, 50% or more, as compared to an effective dose when the therapeutic agent is used alone. In some cases, the therapy may completely substitute a conventional therapy without compromising the outcome of the treatment.

In some embodiments, the subject diagnosed with depression is receiving or has received a prescription anti-depressant therapy, such as an SSRI-based therapy. In certain situations, it is particularly desirable to change the course of the treatment regimen for one reason or another. As described above, for example, in some cases, the subject is a non-responder. In some cases, a subject receiving a conventional therapy may experience adverse side effects such as those listed above that it may be desirable to seek an alternative treatment regimen. Under these circumstances, the subject may gradually shift from the prescription anti-depressant-based therapy to the therapy over a period of time. For example, the subject may receive a gradually increasing proportion of the therapy in conjunction with a gradually decreasing proportion of the conventional therapy until either the adverse side effects lessen or subsides, or until the treatment regimen is completely replaced with the therapy. The changes (e.g., shift) can be made in increments over time, such as weeks to months.

As alluded to above, particularly alarming with respect to a prescription anti-depressant-based therapy is the risk of suicidal ideation. There is a danger that, in some people, anti-depressant treatment will cause an increase, rather than a decrease, in depression. In fact, the U.S. Food and Drug Administration (FDA) requires that all anti-depressant medications include a warning label about the increased risk of suicide in children and young adults, e.g., under the age of 24. The suicide risk is particularly great during the first month to two months of treatment. In 2004, the FDA looked at published and unpublished data on trials of anti-depressants that involved nearly 4,400 children and adolescents. They found that 4 percent of those taking anti-depressants thought about suicide or exhibited emergent suicidal behavior (although no suicides occurred), compared to 2 percent of those receiving placebos (sugar pill).

In response, the FDA decided to adopt a "black box" warning label—the most serious type of warning—on all anti-depressant medications in October of 2004. The warning states that there is an increased risk of suicidal thinking or attempts in children and adolescents taking anti-depressants. Subsequently, in 2007, the FDA proposed that makers of all anti-depressant medications extend the warning to include young adults up through age 24.

Due to the associated risk of suicide, those taking prescription anti-depressants are cautioned to be closely observed for suicidal thoughts and behaviors. Monitoring is said to be especially important if the subject is undergoing depression medication for the first time or if the dose has recently been changed. The patients and family members are generally cautioned for "red flags" such as anxiety, insomnia, hostility, and extreme agitation—particularly if the symptoms appear suddenly or rapidly deteriorate. These risks associated with prescription anti-depressants pose a significant amount of constraints not only on the patients but also on their family members and caretakers. Thus, although results of a comprehensive review of pediatric trials conducted between 1988 and 2006 suggested that the benefits of anti-depressant medications likely outweigh their risks to children and adolescents with major depression and anxiety disorders, there is a strong incentive—and benefit—in reducing these risks by seeking alternative remedies, that are safer but still effective in treating the disorder.

As noted above, one of the risk factors for increased suicidal ideation is the age of the subject. Children and young adults—those under the age of 24 are particularly at risk of developing suicidal thoughts associated with depression, especially when administered an SSRI. Therefore, it is contemplated that in some embodiments the subject in need of treatment for depression and will benefit from the therapy is a human subject of the ages between 6 and 35 diagnosed with a depressive disorder, such as MDD. In some embodiments, the subject is between 9 and 30 years of age. In some embodiments, the subject is between 13 and 24 years of age, such as 13, 14, 15, 16, 17, 18, 19, 20, 21, 22, 23, and 24 years old. In certain embodiments, the subject is 24 years old or younger.

In some embodiments, the subject has been diagnosed with MDD or a related mood disorder, and is receiving or has received a prescription anti-depressant therapy (e.g., an SSRI) and has experienced suicidal ideation or at risk thereof due to factors such as a past history of suicide attempt. In these situations, the subject may benefit from switching to the therapy. Upon determination of such benefits, the subject may gradually (e.g., in increments) replace a prescription anti-depressant drug with the therapy. In some cases, the prescription anti-depressant is over time completely weaned off and is replaced with the therapy. In other cases, the prescription anti-depressant is reduced in dose, frequency or both, but is partially used in combination with the therapy. In other cases, the guardian of a child in whom anti-depressant therapy is contemplated may choose to initially treat the child's depression with the therapy since it is less likely to elicit suicidal ideation.

Thus, as generally described above, the therapy may be used in conjunction with a variety of therapies to enhance therapeutic effects. It is contemplated that the combination of therapeutic substances according to the present disclosure will provide at least the level of efficacy of the commonly used selective serotonin reuptake inhibitor drugs (SSRIs) without being subject to the limitations of that drug class as described above, and may in fact provide greater efficacy through synergy with minimal risk and side effects. Combining drugs which have apparent efficacy as mood stabilizers as well as providing anti-depressant effects may be an alternate mechanism for increased overall efficacy in a heterogeneous population of depressed patients. These therapeutic substances are all generally well tolerated, and with dosages kept below certain milligram amounts, especially with folic acid, the preparation should be able to be made as a formulation available over-the-counter without prescription.

Moreover, as generally described above, in some cases, it may be beneficial to use the therapy in combination with a prescription anti-depressant-based therapy, either as a single composition or as separate compositions administered in conjunction to a subject to treat a neuropsychiatric condition, such as depression. However, the subjects who will benefit from the composition and the methods described herein include those who choose to avoid prescription anti-depressant therapies (such as SSRIs) prone to causing multiple adverse side effects, those who do not respond to a prescription anti-depressant therapy and/or those who experience an adverse side effect or undesired side effect from prescription anti-depressant therapy.

According to certain embodiments, a subject is a human subject suffering from depression, including an MDD or other related mood disorder(s). The subject may or may not be already diagnosed with the condition. However, the subject clinically presents one or more symptoms of depression. Alternatively, the subject has not clinically presented one or more symptoms of the condition but is at risk of developing depression. For example, the subject may have a history of episodes of depression or mood disorders. In some cases, the subject may be genetically predisposed of one or more such disorders. In some cases, the subject is pregnant, plans to become pregnant or is nursing. In some embodiments, suitable subjects include pediatric populations with one or more of the above indicated clinical symptoms or risk. The compositions and methods described herein are particularly useful for treating such a population because most conventional drug therapies available in the market for mood disorders (such as prescription anti-depressant) are not suitable for use for those under the age of 18.

Compositions, Treatment, and Administration

As generally described above, provided herein are methods and compositions involving a specific combination of therapeutic agents: (1) SAMe or a salt thereof; (2) folic acid, or a salt thereof, or active metabolite thereof (e.g., methyl folate or folinic acid or a salt thereof); (3) a compound of Formula (I), or salt thereof; (4) one or more omega fatty acids; and/or (5) vitamin D3. In certain embodiments, this combination is provided in an effective amount. In certain embodiments, this combination is provided in a prophylactically effective amount. Other components, such as Vitamin B12 and/or other anti-depressants, may optionally be added to the therapeutic regimen. In certain embodiments, any one of the compositions described herein is a medical food.

More specifically, in one aspect, provided is a composition comprising S-adenosyl methionine (SAMe), or a salt thereof; and a compound of Formula (I), or salt thereof. In certain embodiments, the composition further comprises folic acid, or a salt thereof, or active metabolite thereof (e.g., methyl folate or folinic acid or a salt thereof). In certain embodiments, the composition further comprises one or more omega-3 fatty acids, or salts thereof. In certain embodiments, the composition further comprises vitamin D3.

In another aspect, provided is a composition comprising folic acid, or a salt thereof, or active metabolite thereof (e.g., methyl folate or folinic acid or a salt thereof); and a compound of Formula (I), or a salt thereof. In certain embodiments, the composition further comprises S-adenosyl methionine (SAMe), or salt thereof. In certain embodiments, the composition further comprises one or more omega-3 fatty acids, or salts thereof. In certain embodiments, the composition further comprises vitamin D3.

In another aspect, provided is a composition comprising one or more omega-3 fatty acids or, salts thereof; and a compound of Formula (I), or a salt thereof. In certain embodiments, the composition further comprises S-adenosyl methionine (SAMe), or salt thereof. In certain embodiments, the composition further comprises folic acid, or a salt thereof, or active metabolite thereof (e.g., methyl folate or folinic acid or a salt thereof). In certain embodiments, the composition further comprises vitamin D3.

In another aspect, provided is a composition comprising vitamin D3; and a compound of Formula (I), or a salt thereof. In certain embodiments, the composition further comprises S-adenosyl methionine (SAMe), or salt thereof. In certain embodiments, the composition further comprises folic acid, or a salt thereof, or active metabolite thereof (e.g., methyl folate or folinic acid or a salt thereof). In certain embodiments, the composition further comprises one or more omega-3 fatty acids, or salts thereof.

In another aspect, provided is a composition comprising a compound of Formula (I), or a salt thereof. In certain embodiments, the composition further comprises folic acid, or a salt thereof, or active metabolite thereof (e.g., methyl folate or folinic acid or a salt thereof). In certain embodiments, the composition further comprises S-adenosyl methionine (SAMe), or salt thereof. In certain embodiments, the composition further comprises one or more omega-3 fatty acids, or salts thereof. In certain embodiments, the composition further comprises vitamin D3.

In certain embodiments, the composition comprises S-adenosyl methionine (SAMe), or a salt thereof; folic acid, or a salt thereof, or active metabolite thereof (e.g., methyl folate or folinic acid or a salt thereof); and a compound of Formula (I), or a salt thereof. In certain embodiments, the composition further comprises one or more omega-3 fatty acids, or salts thereof. In certain embodiments, the composition further comprises vitamin D3. In certain embodiments, the composition consists essentially of S-adenosyl methionine (SAMe), or a salt thereof; folic acid, or a salt thereof, or active metabolite thereof (e.g., methyl folate or folinic acid or a salt thereof); and a compound of Formula (I), or a salt thereof. In certain embodiments, the composition consists essentially of S-adenosyl methionine (SAMe), or a salt thereof; folic acid, or a salt thereof, or active metabolite thereof (e.g., methyl folate or folinic acid or a salt thereof); a compound of Formula (I), or a salt thereof; and one or more omega-3 fatty acids, or salts thereof. In certain embodiments, the composition consists essentially of S-adenosyl methionine (SAMe), or a salt thereof; folic acid, or a salt thereof, or active metabolite thereof (e.g., methyl folate or folinic acid or a salt thereof); a compound of Formula (I), or a salt thereof; one or more omega-3 fatty acids, or salts thereof; and vitamin D3.

In certain embodiments, the one or more omega-3 fatty acids or salts thereof comprises at least 50% EPA. In certain embodiments, the one or more omega-3 fatty acids or salts thereof comprises at least 60% EPA.

In certain embodiments, the composition is formulated for oral administration.

In another aspect, provided is a method of treating a neuropsychiatric condition, the method comprising administering an effective amount of S-adenosyl methionine, or a salt thereof; and a compound of Formula (I), or a salt thereof, to a subject in need thereof. In certain embodiments, the method further comprises administering folic acid, or a salt thereof, or active metabolite thereof (e.g., methyl folate or folinic acid or a salt thereof). In certain embodiments, the method further comprises administering one or more omega-3 fatty acids, or salts thereof. In certain embodiments, the method further comprises administering vitamin D3.

In another aspect, provided is a method of treating a neuropsychiatric condition, the method comprising administering an effective amount of folic acid, or a salt thereof, or active metabolite thereof (e.g., methyl folate or folinic acid or a salt thereof); and a compound of Formula (I):

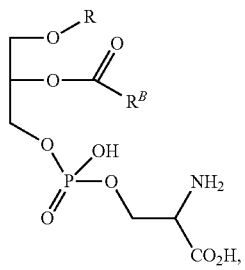

or a salt thereof, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering vitamin D3.

In another aspect, provided is a method of treating a neuropsychiatric condition, the method comprising administering an effective amount of one or more omega-3 fatty acids, or salts thereof; and a compound of Formula (I), or a salt thereof, to a subject in need thereof. In certain embodiments, the method further comprises administering S-adenosyl methionine, or a salt thereof. In certain embodiments, the method further comprises administering vitamin D3. In certain embodiments, the method further comprises administering folic acid, or a salt thereof, or active metabolite thereof (e.g., methyl folate or folinic acid or a salt thereof).

In another aspect, provided is a method of treating a neuropsychiatric condition, the method comprising administering an effective amount of vitamin D3; and a compound of Formula (I), or a salt thereof, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering folic acid, or a salt thereof, or active metabolite thereof (e.g., methyl folate or folinic acid or a salt thereof).

In another aspect, provided is a method of treating a neuropsychiatric condition, the method comprising administering an effective amount of a compound of Formula (I), or a salt thereof, to a subject in need thereof. In certain embodiments, the method further comprises administering S-adenosyl methionine, or a salt thereof. In certain embodiments, the method further comprises administering one or more omega-3 fatty acids, or salts thereof. In certain embodiments, the method further comprises administering folic acid, or a salt thereof, or active metabolite thereof (e.g., methyl folate or folinic acid or a salt thereof). In certain embodiments, the method further comprises administering vitamin D3.

It is contemplated that two or more therapeutic agents described herein may be administered together in the same composition or administered separately in different compositions. In certain embodiments, two of the therapeutic agents are administered together in the same composition, and the other therapeutic agent(s) are administered separately in a different compositions. In certain embodiments, each of the therapeutic agents may be administered separately in different compositions.

Furthermore, any of the compositions described herein may also comprise a prescription anti-depressant, such as selective serotonin reuptake inhibitors (SSRIs), serotonin and dopamine reuptake inhibitors (SDRIs), serotonin-norepinephrine reuptake inhibitors (SNRIs), serotonin-noradrenaline-dopamine reuptake inhibitors (SNDRIs), norepinephrine-dopamine reuptake inhibitors (NDRIs), norepinephrine (noradrenaline) reuptake inhibitors (NRIs), monoamine oxidase inhibitors (MAOIs), selective serotonin reuptake enhancers (SSREs), melatonergic agonists, tryptamines, tricyclic anti-depressants, or atypical ant-depressants, as described herein.

In certain embodiments, the prescription anti-depressant is a selective serotonin reuptake inhibitor (SSRI). In certain embodiments, the SSRI is selected from the group consisting of citalopram, escitalopram, fluoxetine, fluvoxamine, paroxetine, sertraline fenfluramine, norfenfluramine, dapoxetine, femoxetine, and indalpine.

In certain embodiments, the prescription anti-depressant is a dopaminergic anti-depressant. In certain embodiments, the dopaminergic anti-depressant is selected from the group consisting of amineptine, burpoprion, methamphetamine, methylphenidate, nomifensine, pramipexole, ropinirole, and vanoxerine (GBR-12909).

In certain embodiments, the prescription anti-depressant is a serotonin-norepinephrine reuptake inhibitor (SNRI). In certain embodiments, the SNDRI is selected from the group consisting of brasofensine, tesofensine, DOV 21,947 and DOV 102,677.

In certain embodiments, the prescription anti-depressant is a norepinephrine-dopamine reuptake inhibitor (NDRI). In certain embodiments, NDRI is bupropion, reboxetine or radafaxine.

In certain embodiments, the prescription anti-depressant is a monoamine oxidase inhibitor (MAOI). In certain embodiments, the MAOI is selected from the group consisting of isocarboxazid, moclobemide, phenelzine, tranylcypromine, selegiline, emsam, rasagiline, nialamide, iproniazid, iproclozide, toloxatone, linezolid, and Zyvox®.

In certain embodiments, the prescription anti-depressant is a tryptamine.

In certain embodiments, the prescription anti-depressant is a tricyclic anti-depressant having serotonergic activity. In certain embodiments, the tricyclic anti-depressant is selected from clomipramine and amoxapine.

In certain embodiments, the prescription anti-depressant is an agent having serotonergic activity. In certain embodiments, anti-depressant having serotonergic activity is selected from the group consisting of clomipramine, amoxapine, trazadone, olanzapine and ziprasidone.

The composition may optionally comprise a pharmaceutically acceptable excipient. Suitable examples of excipients include, but are not limited to, anti-adherents, binders, coatings, disintegrants, fillers and diluents, flavours, colours, glidants, lubricants, preservatives, sorbents, and sweeteners.

Anti-adherents are generally used to reduce the adhesion between the powder (granules) and the punch faces and thus prevent sticking to tablet punches. Most commonly used is magnesium stearate.

Binders hold the ingredients in a tablet together, and ensure that tablets and granules can be formed with required mechanical strength, and give volume to low active dosis tablets. Exemplary binders include, but are not limited to, starches, sugars, cellulose or modified cellulose such as microcrystalline cellulose, hydroxypropyl cellulose, lactose, or sugar alcohols like xylitol, sorbitol or maltitol. Binders are typically classified according to their application. For example, solution binders are dissolved in a solvent (for example, water or alcohol can be used in wet granulation processes). Non-limiting examples include gelatin, cellulose, cellulose derivatives, polyvinylpyrrolidone, starch, sucrose and polyethylene glycol. By contrast, dry binders are added to the powder blend, either after a wet granulation step, or as part of a direct powder compression formula. Non-limiting examples include cellulose, methyl cellulose, polyvinylpyrrolidone, and polyethylene glycol.

Tablet coatings protect tablet ingredients from deterioration by moisture in the air and make large or unpleasant-tasting tablets easier to swallow. For most coated tablets, a hydroxy propylmethylcellulose (HPMC) film coating is used which is free of sugar and potential allergens. Occasionally, other coating materials are used, for example synthetic polymers, shellac, corn protein zein or other polysaccharides. Capsules are coated with gelatin.

Coatings may be used for purposes of changing the dissolution rates of active species. For examples, enteric coatings can be used to control the rate of drug release and determine where the drug will be released in the digestive tract.

Disintegrants expand and dissolve when wet causing the tablet to break apart in the digestive tract, releasing the active ingredients for absorption. Disintegrant types include water uptake facilitators and tablet rupture promoters. They ensure that when the tablet is in contact with water, it rapidly breaks down into smaller fragments, thereby facilitating dissolution. Examples of disintegrants include, without limitation, crosslinked polyvinyl pyrrolidone, sodium starch glycolate, sodium bicarbonate, and crosslinked sodium carboxymethyl cellulose (crosscarmellose).

Fillers fill out the size of a tablet or capsule, making it practical to produce and convenient for the consumer to use. By increasing the bulk volume, the fillers make it possible for the final product to have the proper volume for patient handling. A suitable filler must be inert, compatible with the other components of the formulation, non-hygroscopic, soluble, relatively inexpensive, compactible, and preferably tasteless or pleasant tasting. For example, plant cellulose (pure plant filler) is a popular filler in tablets or hard gelatin capsules. Dibasic calcium phosphate is another popular tablet filler. A range of vegetable fats and oils can be used in soft gelatin capsules. Other examples of fillers include, without limitation: lactose, sucrose, glucose, mannitol, sorbitol, calcium carbonate, and magnesium stearate.

Flavours can be used to mask unpleasant tasting active ingredients and improve the likelihood that the patient will complete a course of medication. Flavourings may be natural (e.g., fruit extract) or artificial.

Colours are added to improve the appearance of a formulation. Colour consistency is important as it allows easy identification of a medication.

Glidants are used to promote powder flow by reducing interparticle friction and cohesion. These are used in combination with lubricants as they have no ability to reduce die wall friction. Examples include colloidal silicon dioxide, talc, and magnesium carbonate.

Lubricants prevent ingredients from clumping together and from sticking to the tablet punches or capsule filling machine. Lubricants also ensure that tablet formation and ejection can occur with low friction between the solid and die wall. Common minerals like talc or silica, and fats, e.g., vegetable stearin, magnesium stearate or stearic acid are the most frequently used lubricants in tablets or hard gelatin capsules.

Some typical preservatives used in formulations include antioxidants like vitamin A, vitamin E, vitamin C, retinyl palmitate, and selenium; the amino acids cysteine and methionine; citric acid and sodium citrate; and synthetic preservatives such as methyl paraben and propyl paraben.

Sorbents may be used for tablet/capsule moisture-proofing by limited fluid sorbing (taking up of a liquid or a gas either by adsorption or by absorption) in a dry state.

Sweeteners may be added to make the ingredients more palatable, especially in chewable tablets such as antacid or liquids like cough syrup.

Any of the agents described herein can be administered using any amount and any route of administration effective for treatment. The exact amount required will vary from subject to subject, depending on the species, age, and general condition of the subject, the severity of the infection, the particular composition, its mode of administration, its mode of activity, and the like.

Therapeutic agents are typically formulated in dosage unit form for ease of administration and uniformity of dosage. It will be understood, however, that the total daily usage of the compositions will be decided by the attending physician within the scope of sound medical judgment. The specific therapeutically effective dose level for any particular subject will depend upon a variety of factors including the condition being treated and the severity of the condition; the activity of the specific agent employed; the specific composition employed; the age, body weight, general health, sex and diet of the subject; the time of administration, route of administration, and rate of excretion of the specific agent employed; the duration of the treatment; drugs used in combination or coincidental with the specific agent employed; and like factors well known in the medical arts.

Therapeutic agents provided herein can be administered by any route, including oral, intravenous, intramuscular, intra-arterial, intramedullary, intrathecal, subcutaneous, intraventricular, transdermal (e.g., patches), interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent, the condition of the subject (e.g., whether the subject is able to tolerate oral administration), etc. The preferred route of administration is oral administration.

The exact amount of an agent required to achieve a therapeutically effective or prophylactically effective amount will vary from subject to subject, depending, for example, on species, age, and general condition of a subject, severity of the side effects or condition, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

For example, in a non-limiting embodiment, the therapy may be formulated as one or more tablets or capsules for oral administration. For instance, a tablet or capsule may contain one or more of the following components such that the components are administered together, either in one or more compositions, as part of the therapy:

(1) about 200 mg to about 2000 mg of SAMe, or a salt thereof (e.g., about 400 mg to about 1600 mg, or about 800 mg to about 1600 mg of SAMe or a salt thereof);
(2) about 0.5 mg to about 5 mg of folic acid, or a salt thereof (e.g., about 1 mg to about 3 mg of folic acid or a salt thereof); and/or about 5 mg to about 45 mg of methyl folate, or a salt thereof (e.g., about 5 mg to about 20 mg of methyl folate or a salt thereof) and/or about 5 mg to about 15 mg of folinic acid, or a salt thereof (e.g., about 5 to about 10 mg of folinic acid, or a salt thereof); and
(3) about 50 mg to about 1000 mg of a compound of Formula (I), or salt thereof;
(4) about 500 mg to about 5 g of one or more omega-3 fatty acids, or salts thereof, e.g., rich in EPA (e.g., about 800 mg to about 1600 mg of one or more omega-3 fatty acids, or salts thereof, rich in EPA); and/or
(5) about 500 IU to about 2000 IU, inclusive, of vitamin D3.

In certain preferred embodiments, a tablet or capsule may contain one or more of the following components such that the components are administered together, either in one or more compositions, as part of the therapy:

(1) about 200 mg to about 2000 mg of SAMe, or a salt thereof (e.g., about 400 mg to about 1600 mg, or about 800 mg to about 1600 mg of SAMe, or a salt thereof);
(2) about 5 mg to about 45 mg of methyl folate, or a salt thereof (e.g., about 5 to about 20 mg of methyl folate, or a salt thereof);
(3) about 50 mg to about 500 mg of a compound of Formula (I), or salt thereof;
(4) about 500 mg to about 5 g of one or more omega-3 fatty acids, or salts thereof, e.g., rich in EPA (e.g., about 800 mg to about 1600 mg of one or more omega-3 fatty acids, or salts thereof, rich in EPA); and/or
(5) about 800 IU to about 1200 IU, inclusive, of vitamin D3.

The therapy may be administered once, twice or three times daily, depending on total recommended daily dosage of the therapy combination, the subject, and the condition to be treated. For example, a subject in need may take the therapy 1 to 6 times daily, for example, 1, 2, 3, 4, 5, 6 times daily, depending on the body weight, age, and other clinical criteria.

Kits

The therapy described herein is readily adaptable for distribution in the form of a kit. A kit is typically packaged individually in a container. A kit may include each of the therapy components described herein premeasured and/or mixed together in a fashion convenient for administration, e.g., formulated into one or more capsules, tablets, syrup, transdermal patches, etc. The kit typically includes instructions for use, which may be on a separate piece of medium (e.g., on a sheet of paper), or printed upon a container itself, or on the surface of a package. Alternatively, or in addition, the instructions may be made available separately via, for example, online sources. The kit comprises at least one unit dosage form of the composition. Typically, however, the kit contains a supply of the therapy to be taken for a predetermined duration of time, e.g., a 7-day supply, 14-day supply, 30-day supply, 60-day supply, or 90-day supply of the therapy.

In some embodiments, the kit also includes prescribing information.

ADDITIONAL DEFINITIONS

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Comprising," "consisting of," and "consisting essentially of", when used in the claims, shall have its ordinary meaning as used in the field of patent law.

As used herein, the term "salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

A "subject" to which administration is contemplated includes, but is not limited to, a mammal, including humans (i.e., a male or female of any age group, e.g., a pediatric subject (e.g, infant, child, adolescent) or adult subject (e.g., young adult, middle-aged adult or senior adult)), other primates (e.g., cynomolgus monkeys, rhesus monkeys); commercially relevant mammals such as cattle, pigs, horses, sheep, and goats; and domestic mammals such as cats and dogs. The subject may also be a pregnant female.

As used herein, the terms "condition," "disease," and "disorder" are used interchangeably to refer to an impaired biological, clinical, and/or psychiatric condition in a subject.

The terms "substance," "drug," "agent," "therapeutic," "therapeutic agent," "medicine," and "medicament" are used interchangeably herein.

The terms "treating," "treatment," and "promotion," are used herein to mean providing a subject in need with a "therapy" to obtain all or any of the desired results of a therapy. The term "therapy" as used herein generally means any biological or psychiatric application or treatment used to obtain a desired pharmacologic, biologic, physiologic and/or psychologic effect. The effect may be prophylactic in terms of completely or partially preventing a disease or symptom thereof and/or may be therapeutic in terms of a partial or complete cure for a disease and/or adverse effect attributable to the disease. Therapeutic effects shall include: (a) preventing a condition from occurring in a subject which may be predisposed to the condition but has not yet been diagnosed as having it; (b) inhibiting a condition, i.e., arresting its development; and/or (c) relieving a condition, i.e., causing regression of the condition.

As used herein, unless otherwise specified, the terms "prevent," "preventing" and "prevention" contemplate an action that occurs before a subject (e.g., such as a pregnant subject) begins to suffer from the condition, which inhibits or reduces the severity of the condition.

As used herein, and unless otherwise specified, the terms "manage," "managing" and "management" encompass preventing the recurrence of the condition in a subject who has already suffered from the condition. The terms encompass modulating the threshold, development and/or duration of the condition, and/or changing the way that a subject responds to the condition.

In general, the "effective amount" of a compound refers to an amount sufficient to elicit the desired biological response. As will be appreciated by those of ordinary skill in this art, the effective amount of a compound may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of an agent or combination of agents is an amount sufficient to provide a therapeutic benefit in the treatment or management of a condition, or to delay or minimize one or more symptoms associated with the condition. A therapeutically effective amount of an agent or combination of agents means an amount of the therapeutic agent, alone or in combination with other therapies, which provides a therapeutic benefit in the treatment or management of the condition. The term "therapeutically effective amount" can encompass an amount that improves overall therapy, reduces or avoids symptoms or causes of the condition, or enhances the therapeutic efficacy of another therapeutic agent.

As used herein, a "prophylactically effective amount" of an agent or combination of agents is an amount sufficient to prevent a condition, or one or more symptoms associated with the condition, or prevent its recurrence. A prophylactically effective amount of an agent or combination of agents means an amount of therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, "suffer", "suffers," "suffering from" or "having" refers to a subject diagnosed with a condition. As used herein, "likely to suffer from" or "likely to have" refers to a subject who has not been diagnosed with a particular condition by a medical practitioner, but has a predisposition for (e.g., genetic and/or physiologic predisposition), or exhibits signs or symptoms of, the condition.

As used herein, "in combination" or "in conjunction" (as in "administered in conjunction with" or "administered together") refers to the combining of two or more of the agents such that the therapeutic effects from the agents are overlapping in time and/or target (e.g., cells, tissues) in vivo. In some embodiments, the two or more agents are administered together in the same composition. In some embodiments, the two or more agents are administered together in separate compositions (i.e., "administered separately"). In certain embodiments, the two or more agents are administered together at the same time (i.e., "administered simultaneously"). In certain embodiments, the two or more agents are administered together one after the other (i.e., "administered sequentially").

It should also be understood that, unless clearly indicated to the contrary, in any methods claimed herein that include more than one act, the order of the acts of the method is not necessarily limited to the order in which the acts of the method are recited.

Each of the foregoing patents, patent applications and references that are recited in this application are herein incorporated in their entirety by reference, particularly for the teaching referenced herein.

REFERENCES

Knowlton, L. and Staff G. T. (2001) Investigating SAM-e. *Geriatric Times* II(5) http://www.geriatrictimes.com/g010923.html. Retrieved 2006 Dec. 8.

Kagan, B. L., Sultzer, D. L., Rosenlicht, N.; Gerner, R. H. (May 1, 1990) Oral S-adenosylmethionine in depression: a randomized, double-blind, placebo-controlled trial. *Am J Psychiatry* 147(5):591-595.

Rosenbaum, J. F., Fava, M., Falk, W. E., Pollack, M. H., Cohen, L. S. Cohen, B. M., Zubenko, G. S. (May 1990) The anti-depressant potential of oral S-adenosyl-1-methionine. *Acta Psychiatrica Scandinavica* 81(5):432-436.

Morrison, L. D., Smith, D. D., Kish, S. J. (1996) Brain S-adenosylmethionine levels are severely decreased in Alzheimer's disease. *J Neurochem.* 67(3):1328-1331.

Bottiglieri, T. (1997) Ademetionine (S-adenosylmethionine) neuropharmacology: implications for drug therapies in psychiatric and neuropsychiatric disorders. *Expert Opin Investig Drugs* 6(4):417-426.

Najm, W. I., Reinsch, S., Hoehler, F., Tobis, J. S., Harvey, P. W. (February 2004) S-adenosyl methionine (SAMe) versus celecoxib for the treatment of osteoarthritis symptoms: a double-blind cross-over trial [ISRCTN36233495]. *BMC Musculoskelet Disord* 5(6) Abstract.

S-Adenosylmethionine (SAMe). University of Maryland Medical Center. 2004.

Mischoulon, D., Fava, M. (November 2002) Role of S-adenosyl-L-methionine in the treatment of depression: a review of the evidence. *Am J Clin Nutr* 76(5):1158S-1161S.

Ural, Serdar H. (2008-11) Folic Acid and Pregnancy. *Kid's Health.* http://kidshealth.org/parent/pregnancy_newborn/pregnancy/folic_acid.html.

Bailey, S. W., Ayling, J. E. (2009) The extremely slow and variable activity of dihydrofolate reductase in human liver and its implications for high folic acid intake. *Proc Natl Acad Sci USA.* 106:15424-15429.

Weinstein, S. J. et al (November 2003) Null Association Between Prostate Cancer and Serum Folate, Vitamin B6, Vitamin B12, and Homocysteine. *Cancer Epidemiology, Biomarkers, & Prevention* 12:1271-1272.

Ontario, Eat Right Ontario. Government of Ontario www.eatrightontario.ca/en/ViewDocument.aspx?id=109

Coppen, A., Bolander-Gouaille, C. (2005) Treatment of depression: time to consider folic acid and vitamin B12. *Journal of Psychopharmacology* 19(1):59-65.

Taylor, M. J., Carney, S. M., Goodwin, G. M., Geddes, J. R. (2004) Folate for depressive disorders: systematic review and meta-analysis of randomized controlled trials. *Journal of Psychopharmacology* 18(2):251-256.

Gilbody, S., Lewis, S., Lightfoot, T. (January 2007) Methylenetetrahydrofolate reductase (MTHFR) genetic polymorphisms and psychiatric disorders: a HuGE review. *American Journal of Epidemiology* 165(1):1-13.

Su, K-P, Huang, S-Y; Chiub, C-C, Shenc, W. W. (2003) Omega-3 fatty acids or salts thereof in major depressive disorder: A preliminary double-blind, placebo-controlled trial. *Eur Neuropsychopharmacol* 13(4):267-271.

Naliwaiko, K., Araújo, R. L., da Fonseca, R. V., Castilho, J. C., Andreatini, R., Bellissimo, M. I., Oliveira, B. H., Martins, E. F., Curi, R., Fernandes, L. C., Ferraz, A. C. (April 2004) Effects of fish oil on the central nervous system: a new potential anti-depressant? *Nutritional Neuroscience* 7(2):91-99.

Green, P., Hermesh, H., Monselisec, A., Maromb, S., Presburgerb, G., Weizman, A. (2006) Red cell membrane omega-3 fatty acids or salts thereof are decreased in non-depressed patients with social anxiety disorder. *Eur Neuropsychopharmacol* 16(2):107-113.

Yehuda, S., Rabinovitz, S., Mostofsky, D. I. (2005) Mixture of essential fatty acids lowers test anxiety. *Nutritional Neuroscience* 8(4):265-267.

Nemets, B., Stahl, Z., Belmaker, R. H. (2002) Addition of omega-3 fatty acid to maintenance medication treatment for recurrent unipolar depressive disorder. *Am J Psychiatry* 159(3):477-479.

Iso, H., Rexrode, K. M., Stampfer, M. J., Manson, J. E., Colditz, G. A., Speizer, F. E. Hennekens, C. H., Willett, W. C. (2001) Intake of fish and omega-3 fatty acids or salts thereof and risk of stroke in women. *JAMA* 285(3):304-312.

The U.S. Food and Drug Administration classification—GRAS (Generally Recognized as Safe)

Trivedi, B. (2006 Sep. 23) The good, the fad, and the unhealthy. *New Scientist* 42-49.

Calabrese, J. R., Rapport, D. J., Shelton, M. D. (1999) Fish oils and bipolar disorder: A promising but untested treatment. *Arch Gen Psychiatry* 56(5):413-414.

Stoll, A. L., et al. (1999) Omega 3 fatty acids in bipolar disorder: A preliminary double-blind, placebo-controlled trial. *Arch Gen Psychiatry* 56(5):407-412.

Nemets, H., Nemets, B., Apter, A., Bracha, Z., Belmaker, R. H. (2006) Omega-3 treatment of childhood depression: A controlled, double-blind pilot study. *Am J Psychiatry* 163 (6):1098-1100.

Huan, M. et al. (2004) Suicide attempt and n-3 fatty acid levels in red blood cells: a case control study in China. *Biol Psychiatry* 56(7):490-496.

Freeman, M. P., Hibbeln, J. R., Wisner, K. L., et al. (2006) Omega-3 fatty acids or salts thereof: evidence basis for treatment and future research in psychiatry. *J Clin Psychiatry* 67(12):1954-1967.

Lin, P-Y, Kuan-P. S. (July 2007) A Meta-Analytic Review of Double-Blind, Placebo-Controlled Trials of Anti-depressant Efficacy of Omega-3 fatty acids or salts thereof. *J Clin Psychiatry* 68(7):1056-1061.

Mischoulon, D., Papakostas, G. I., Dording, C. M., et al. (2009 Aug. 25) A double-blind, randomized controlled trial of ethyl-eicosapentaenoate for major depressive disorder. *J Clin Psychiatry Abstract*.

Omega-e Fatty Acids in Mood Disorders. (November 2009) *Psychiatry Drug Alerts* XXIII(11).

Quetiapine/Ritonavir: Clinically Significant Interaction. (December 2009) *Psychiatry Drug Alerts*. XXIII(12).

Behzadi, A. H. et al., 2009 Folic acid efficacy as an alternative drug added to sodium valproate in the treatment of acute phase of mania in bipolar disorder: a double-blind randomized controlled trial. *Acta Psychiatrica Scandinavica* 1-5.

Stahl, S. M. (September 2008) L-Methylfolate: A Vitamin for Your Monoamines. *J. Clin Psychiatry* 69(9):1352-1353.

Farah, A. (January 2009) The Role of L-Methylfolate in Depressive Disorders. *Primary Psychiatry* 16(1) (Suppl 1):2-7.

Shelton, R. C., (January 2009) Commentary. *Primary Psychiatry* 16(1) (Suppl 1):8.

Stahl, S. M. (October 2007) Novel Therapeutics for Depression: L-methylfolate as a Trimonoamine Modulator and Anti-depressant-Augmenting Agent. *CNS Spectrums* 12(10):739-744.

Freeman, M. P. (2009) Complementary and Alternative Medicine (CAM): Considerations for the Treatment of Major Depressive Disorder. *J. Clin Psychiatry* 70 (Suppl 5):4-6.

Freeman, M. P. (2009) Omega-3 fatty acids or salts thereof in Major Depressive Disorder. *J. Clin Psychiatry* 70 (Suppl 5):7-11.

Fava, M. and Mischoulon D. (2009) Folate in Depression: Efficacy, Safety, Differences in Formulations, and Clinical Issues. *J. Clin Psychiatry* 70 (Suppl 5):12-17.

Papakostas, G. I. (2009) Evidence for S-Adenosyl-L-Methionine (SAM-e) for the Treatment of Major Depressive Disorder. *J. Clin Psychiatry* 70 (Suppl 5):18-22.

Shelton, R. C. (2009) St. John's Wort (*Hypericum perforatum*) in Major Depression. *J. Clin Psychiatry* 70 (Suppl 5):23-27.

Mischoulon, D. et al. (December 2009) A Double-Blind, Randomized Controlled Trial of Ethyl-Eicosapentaenoate for Major Depressive Disorder." *J. Clin Psychiatry* 70(12): 1636-1644.

Other Embodiments

All patents, patent applications, and literature references cited herein are incorporated herein by reference.

The foregoing has been a description of certain non-limiting embodiments. Those of ordinary skill in the art will appreciate that various changes and modifications to this description may be made without departing from the spirit or scope of the present disclosure, as defined in the following claims.

What is claimed is:

1. A method of treating a neuropsychiatric condition, or for promoting wellness and/or energy, the method comprising administering an effective amount of S-adenosyl methionine (SAMe), or a salt thereof; methyl folate, or a salt thereof; and a compound of Formula (I):

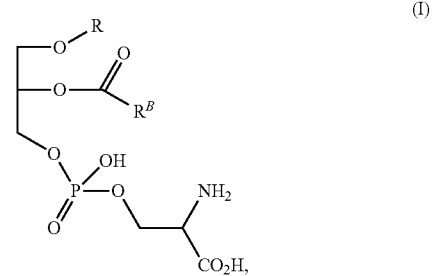

or a salt thereof, wherein:

R is hydrogen or —C(=O)$R^A$, wherein $R^A$ is unsubstituted $C_{10-18}$ alkyl; and —C(=O)$R^B$ is of the formula:

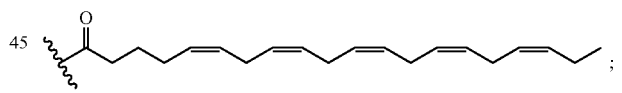

to a subject in need thereof.

2. The method of claim 1, wherein the compound of Formula (I) is of the formula:

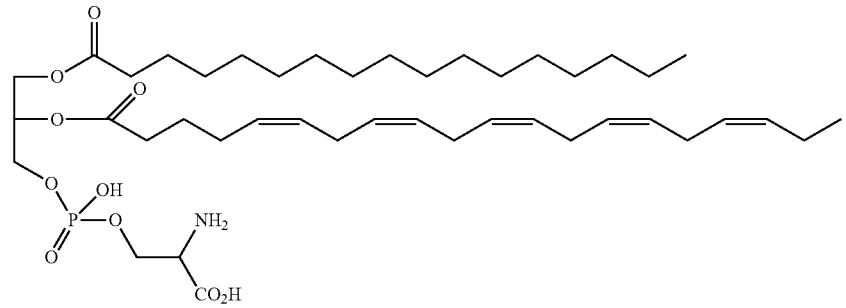 [SMILES: CC/C=C\C/C=C\C/C=C\C/C=C\C/C=C\CCCC(=O)OC(COC(=O)CCCCCCCCCCCCCCCC)COP(=O)(O)OCC(N)C(=O)O]

or a salt thereof.

3. The method of claim 1, wherein the compound of Formula (I), or salt thereof, is provided in a range of between about 50 mg to about 1000 mg, inclusive.

4. The method of claim 1, wherein S-adenosyl methionine, or a salt thereof, is provided in a range of between about 200 mg to about 2000 mg, inclusive.

5. The method of claim 1, wherein methyl folate, or a salt thereof, is provided in a range of between about 1 mg to about 45 mg, inclusive.

6. The method of claim 1, further comprising administering one or more omega-3 fatty acids, or salts thereof.

7. The method of claim 6, wherein one or more omega-3 fatty acids, or salts thereof, is provided in a range of between about 500 mg to about 5 g, inclusive.

8. The method of claim 6, wherein the one or more omega-3 fatty acids, or salts thereof, comprises at least 50% EPA.

9. The method of claim 1, further comprising administering vitamin D3.

10. The method of claim 9, wherein the vitamin D3 is provided in a range of about 500 IU to about 2000 IU, inclusive.

11. The method of claim 1, further comprising administering vitamin $B_{12}$.

12. The method of claim 1, wherein S-adenosyl methionine (SAMe), or a salt thereof; methyl folate, or a salt thereof; and a compound of Formula (I), or a salt thereof, are each administered separately in different compositions.

13. The method of claim 1, wherein S-adenosyl methionine (SAMe), or a salt thereof; methyl folate, or a salt thereof; and a compound of Formula (I), or a salt thereof, are administered together in the same composition.

14. The method of claim 1, wherein the neuropsychiatric condition is selected from mood disorders or conditions characterized by atypical mood.

15. The method of claim 14, wherein the mood disorders are selected from the group consisting of depression, Bipolar Disorder, and Anxiety Disorder.

16. The method of claim 15, wherein the depression is Major Depressive Disorder.

17. The method of claim 14, wherein the condition characterized by atypical mood is selected from the group consisting of stress, hormonal mood swings, Mild Cognitive Impairment, substance-induced mood disorders, dementia, Alzheimer's disease, Parkinson's disease, Huntington's disease, and psychotic disorders.

18. The method of claim 17, wherein the hormonal mood swings are mood swings during pregnancy, during postpartum, during puberty, or during menopause, or are a result of a Premenstrual Dysphoric Disorder condition.

19. The method of claim 17, wherein the psychotic disorder is selected from the group consisting of Schizoaffective Disorder, Schizophrenia, Delusional Disorder, and Psychotic Disorder Not Otherwise Specified.

20. The method of claim 1, wherein the method is for treating depression.

21. The method of claim 1, wherein the compound of Formula (I), or salt thereof, is provided in a range of between about 100 mg to about 500 mg, inclusive.

* * * * *

UNITED STATES PATENT AND TRADEMARK OFFICE
CERTIFICATE OF CORRECTION

PATENT NO. : 11,110,113 B2  
APPLICATION NO. : 16/347156  
DATED : September 7, 2021  
INVENTOR(S) : Alexander Vuckovic Page 1 of 1

It is certified that error appears in the above-identified patent and that said Letters Patent is hereby corrected as shown below:

In the Claims

In Claim 2, at Column 50, Lines 52-67, the following chemical structure:

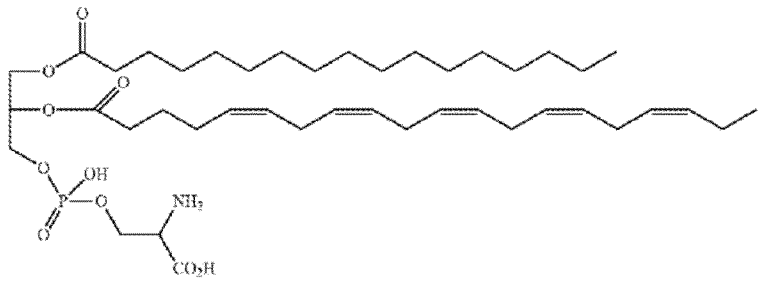

Should be replaced with:

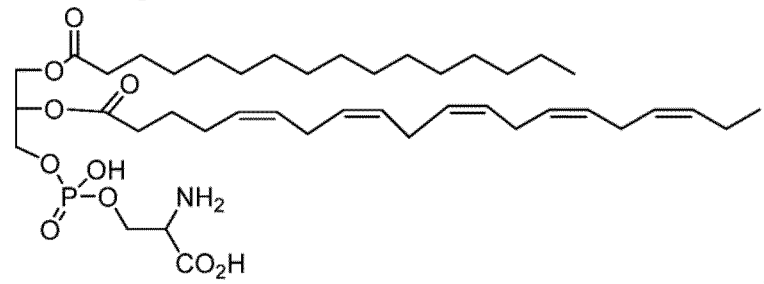

Signed and Sealed this  
Second Day of November, 2021

Drew Hirshfeld  
*Performing the Functions and Duties of the*  
*Under Secretary of Commerce for Intellectual Property and*  
*Director of the United States Patent and Trademark Office*